United States Patent
Bowler

(10) Patent No.: US 9,952,225 B2
(45) Date of Patent: Apr. 24, 2018

(54) METHODS FOR DETECTION OF RESPIRATORY DISEASES

(71) Applicant: NATIONAL JEWISH HEALTH, Denver, CO (US)

(72) Inventor: Russell P. Bowler, Denver, CO (US)

(73) Assignee: National Jewish Health, Denver, CO (US)

( * ) Notice: Subject to any disclaimer, the term of this patent is extended or adjusted under 35 U.S.C. 154(b) by 0 days.

(21) Appl. No.: 15/113,593

(22) PCT Filed: Jan. 23, 2015

(86) PCT No.: PCT/US2015/012666
§ 371 (c)(1),
(2) Date: Jul. 22, 2016

(87) PCT Pub. No.: WO2015/112848
PCT Pub. Date: Jul. 30, 2015

(65) Prior Publication Data
US 2017/0003300 A1    Jan. 5, 2017

Related U.S. Application Data

(60) Provisional application No. 61/931,449, filed on Jan. 24, 2014.

(51) Int. Cl.
*G01N 33/68* (2006.01)
(52) U.S. Cl.
CPC ... *G01N 33/6893* (2013.01); *G01N 2800/122* (2013.01); *G01N 2800/50* (2013.01)
(58) Field of Classification Search
None
See application file for complete search history.

(56) References Cited

U.S. PATENT DOCUMENTS

| | | | |
|---|---|---|---|
| 2008/0044843 A1 | 2/2008 | Perlee et al. | |
| 2013/0149389 A1 | 6/2013 | Flora et al. | |

FOREIGN PATENT DOCUMENTS

| | | |
|---|---|---|
| WO | WO 2006/105252 | 10/2006 |
| WO | WO 2011/044508 | 4/2011 |
| WO | WO 2013/182725 | 12/2013 |

OTHER PUBLICATIONS

Alexiou et al. "RAGE: A Multi-Ligand Receptor Unveiling Novel Insights in Health and Disease," Current Medicinal Chemistry, 2010, vol. 17, pp. 2232-2252.
Bafadhel et al. "Acute Exacerbations of Chronic Obstructive Pulmonary Disease: Identification of Biologic Clusters and Their Biomarkers," Am J respir Crit Care Med, Jun. 2011, vol. 184, pp. 662-671.
Basili et al. "Lipoprotein(a) serum levels in patients affected by chronic obstructive pulmonary disease," Atherosclerosis, Dec. 1999, vol. 147, pp. 249-252.
Bowler "Surfactant Protein D as a Biomarker for Chronic Obstructive Pulmonary Disease," COPD, 2012, vol. 9, pp. 651-653.
Brightling "Biomarkers that Predict and Guide Therapy for Exacerbations of Chronic Obstructive Pulmonary Disease," Annals of the American Thoracic Society, 2013, vol. 10 Supplement, pp. S214-S219.
Buckley et al. "The Receptor for Advanced Glycation End Products (RAGE) and the Lung," Journal of Biomedicine and Biotechnology, 2010, vol. 2010, Article ID 917108, 11 pages.
Cockayne et al. "Systemic Biomarkers of Neutrophilic Inflammation, Tissue Injury and Repair in COPD Patients with Differing Levels of Disease Severity," PLOS One, Jun. 2012, vol. 7, No. 6, e38629, 12 pages.
Dickens et al. "COPD association and repeatability of blood biomarkers in the ECLIPSE cohort," Respiratory Research, 2011, vol. 12, p. 146.
Faner et al. "Lessons from ECLIPSE: a review of COPD biomarkers," Thorax, 2014, vol. 69, No. 7, pp. 666-672.
Gaki et al. "Associations between BODE Index and Systemic Inflammatory Biomarkers in COPD," Journal for Chronic Obstructive Pulmonary Disease, Dec. 2011, vol. 8, No. 6, pp. 408-413.
Gao et al. "Sputum Inflammatory Cell-Based Classification of Patients with Acute Exacerbation of Chronic Obstructive Pulmonary Disease," PLOS One, May 2013, vol. 8, No. 5, e57678, 8 pages.
Gerritsen et al. "Markers of inflammation and oxidative stress in exacerbated chronic obstructive pulmonary disease patients," Respiratory Medicine, 2005, vol. 99, pp. 84-90.
Hertzen et al. "Chlamydia pneumoniae infection in patients with chronic obstructive pulmonary disease," Epidemiology and Infection, 1997, vol. 118, pp. 155-164.
Karadag et al. "Biomarkers of Systemic Inflammation in Stable and Exacerbation Phases of COPD," Lung, 2008, vol. 186, pp. 403-409.
Lopez-Campos et al. "Increased levels of soluble ICAM-1 in chronic obstructive pulmonary disease and resistant smokers are related to active smoking," Biomarkers Med. 2012, vol. 6, No. 6, pp. 805-811.
Merali et al. "Analysis of the Plasma Proteome in COPD: Novel Low Abundance Proteins Reflect the Severity of Lung Remodeling," COPD, Apr. 2014, vol. 11, No. 2, pp. 177-189.
Miniati et al. "Soluble receptor for advanced glycation end products in COPD: relationship with emphysema and chronic cor pulmonale: a case-control study," Respiratory Research, 2011, vol. 12, 37, 9 pages.

(Continued)

*Primary Examiner* — Heidi Reese
(74) *Attorney, Agent, or Firm* — Sheridan Ross P.C.

(57) ABSTRACT

Disclosed are methods of identifying, predicting and treating subjects at risk for exacerbation or the presence of a respiratory disease, by detecting expression levels of one or more proteins associated with the respiratory disease, wherein said one or more proteins is selected from the group of CCL24, IL2RA, APOA4, GC, IgA, LPA, KLK3 F, FAS, NRCAM, TNFRSFIOC, IL12B, IL23A, RAGE, CCL20, ICAM1, SERPINA7, CDH13 and CDH1, and wherein said respiratory disease may be chronic obstructive pulmonary disease or emphysema.

2 Claims, 9 Drawing Sheets

(56) References Cited

OTHER PUBLICATIONS

O'Neal et al. "Comparison of serum, EDTA plasma and P100 plasma for luminex-based biomarker multiplex assays in patients with chronic obstructive pulmonary disease in the SPIROMICS study," Journal of Translational Medicine, 2014, vol. 12, 9, 9 pages.

Rosenberg et al. "Biomarkers in chronic obstructive pulmonary disease," Tranlsational Research, Apr. 2012, vol. 159, No. 4, pp. 228-237.

Singh et al. "Sputum neutrophils as a biomarker in COPD: findings from the Eclipse study," Respiratory Research, Jun. 2010, vol. 11, 77, 12 pages.

Smith et al. "Reduced soluble receptor for advanced glycation end-products in COPD," European Respiratory Journal, 2011, vol. 37, No. 3, pp. 516-522.

Thomsen et al. "Inflammatory Biomarkers and Comorbidities in Chronic Obstructive Pulmonary Disease," Am J Respir Crit Care Med, Nov. 2012, vol. 186, No. 10, pp. 982-988.

Thomsen et al. "Inflamatory Biomarkers and Exacerbations in Chronic Obstructive Pulmonary Disease," JAMA, Jun. 2013, vol. 309, No. 22, pp. 2353-2361.

Tzortzaki et al. "Laboratory markers for COPD in "susceptible" smokers," Clinica Chimica Acta, 2006, vol. 364, pp. 124-138.

Uchida et al. "Receptor for Advanced Glycation End-Products Is a Marker of Type I Cell Injury in Acute Lung Injury," Am J Respir Crit Care Med, 2006, vol. 173, pp. 1008-1015.

Wu et al. "Advanced glycation end products and its receptor (RAGE) are increased in patients with COPD," Respiratory Medicine, 2011, vol. 105, pp. 329-336.

York et al. "High-resolution mass spectrometry proteomics for the identification of candidate plasma protein biomarkers for chronic obstructive pulmonary disease," Biomarkers, 2010, vol. 15, No. 4, pp. 367-377.

International Search Report and Written Opinion for International (PCT) Patent Application No. PCT/US2015/012666, dated Jun. 10, 2015 18 pages.

International Preliminary Report on Patentability for International (PCT) Patent Application No. PCT/US2015/012666, dated Aug. 4, 2016 10 pages.

METHODS FOR DETECTION OF RESPIRATORY DISEASES

CROSS REFERENCE TO RELATED APPLICATIONS

This application is a national stage application under 35 U.S.C. 371 of PCT Application No. PCT/US2015/012666, having an international filing date of Jan. 23, 2015, which designated the U.S., which claims the benefit of priority under 35 U.S.C. 119(e) to U.S. Provisional Patent Application No. 61/931,449, filed Jan. 24, 2014. The disclosure of U.S. Provisional Patent Application No. 61/931,449, and PCT Application No. PCT/US2015/012666 are incorporated herein by reference in their entirety.

GOVERNMENT RIGHTS

This invention was made with Government support under grant number RO1 HL 09-5432-01, awarded by the National Institutes of Health (NIH). The Government has certain rights in the invention.

FIELD OF THE INVENTION

The present invention generally relates to methods of identifying, predicting and treating subjects at risk for exacerbation of a respiratory disease as well as identifying, predicting and treating subjects at risk of developing a respiratory disease by detecting expression levels of one or more proteins associated with the respiratory disease.

BACKGROUND OF THE INVENTION

Chronic Obstructive Pulmonary Disease (COPD) is a major cause of outpatient medical care, hospital admission days and mortality (Vestbo, J., et al. Global Strategy for the Diagnosis, Management and Prevention of Chronic Obstructive Pulmonary Disease, GOLD Executive Summary. *Am J Respir Crit Care Med* (2012)). Acute episodes of worsening COPD are characterized by cough, sputum production, shortness of breath and wheezing (often referred to as acute exacerbations of COPD or AECOPD) and are treated with antibiotics and/or prednisone. Although the major risk factor for COPD is a history of smoking, most current and former smokers do not have COPD. Furthermore, smokers without COPD have acute episodes of airway disease clinically identical to exacerbations of COPD (often referred to as acute bronchitis).

Recent work suggests that there are subsets of current and former smokers who are more susceptible to frequent episodes of chronic bronchitis or acute exacerbations of COPD (Hurst, J. R., et al. Susceptibility to exacerbation in chronic obstructive pulmonary disease. *N Engl J Med* 363, 1128-1138 (2010)). Clinical predictors for these episodes include: previous episodes of bronchitis or exacerbations of COPD, airflow obstruction on spirometry, low respiratory health scores, and gastroesophageal reflux (Hurst, J. R., et al. Susceptibility to exacerbation in chronic obstructive pulmonary disease. *N Engl J Med* 363, 1128-1138 (2010)). These susceptible patients are also postulated to be more prone to systemic inflammation. Evidence for systemic inflammation from previous large studies includes: elevated white blood cell count and fibrinogen (Thomsen, M., et al. Inflammatory biomarkers and exacerbations in chronic obstructive pulmonary disease. *Jama* 309, 2353-2361 (2013)), and C reactive Protein (CRP). These studies did not include at risk current and former smokers and were limited to the study of a small number of biomarkers. Other studies have suggested biomarkers such as surfactant protein D (Ozyurek, B A., et al. *Multidisciplinary respiratory medicine,* 2013; 8:36), fetuin A (Minas, M., et al., *COPD* 2013, 10:28-34, adiponectin and CRP (Kirdar, S., et al. *Scandinavian Journal of Clinical and Laboratory Investigation,* 2009; 69: 219-224) might be predictive of AECOPDs. These studies have been limited by small sample size and limited clinical phenotyping with incomplete adjustment for covariates predictive of exacerbations.

The presence of emphysema has been associated with increased mortality and increased risk of lung cancer in COPD. Similarly, the distribution of emphysema is important for determining patients eligible for lung volume reduction procedures. High resolution computed tomography (HRCT) chest scans are useful in characterizing the distribution of emphysema and providing quantitative measurements, however they are expensive, may require a separate patient visit and raise concerns about radiation exposure.

At present, there exists a need for development of reliable and sensitive molecular markers which can be used to predict subjects who are susceptible to exacerbation of COPD as well as the presence or absence of emphysema.

BRIEF DESCRIPTION OF THE DRAWINGS

FIG. 3A shows advanced glycosylation end-product receptor (RAGE). FIG. 3B shows Intracellular adhesion molecule 1 (ICAM1). FIG. 3C shows Cadherin 1 (CDH1), FIG. 3D shows Cadherin 13 (CDH13) and FIG. 3E shows thyroxin-binding globulin (SERPINA7). The results presented are normal quantile transformed biomarker levels on the ordinate and percent emphysema (% low attenuation ≤-950 HU) on CT scan on abscissa ($p<0.001$ for all comparisons).

(FIG. 4B) same covariates with $FEV_1$ and 15 biomarkers; (FIG. 4C) covariates with $FEV_1$ (≥50% predicted) and (FIG. 4D) covariates with $FEV_1$ (≥50% predicted) and 15 biomarkers. The results presented are ROC curves for covariates age, gender, body mass index, current smoking status with $FEV_1$ (all ranges and excluding severe and very severe airflow limitation) with and without 15 biomarkers from the multiple regression model (RAGE, ICAM1, CCL20, SERPINA7, CDH13, CDH1, TGFB1 LAP, CCL13, TNFRSF11B, CCL8, IgA, SORT1, IL2RA, CCL2, IL12B) as labeled FIGS. 4A-4D. Nominal logistic regression was performed to derive the ROC curves with emphysema compared to no emphysema as the outcome. Emphysema was considered present if % LAA<-950 HU was ≥5% and emphysema was absent if % LAA<-950 HU<5%. AUC=Area under curve. For FIG. 4A the AUC was 0.88; for FIG. 4B the AUC was 0.92; for FIG. 4C the AUC was 0.78 and for FIG. 4D the AUC was 0.85.

SUMMARY OF THE INVENTION

Figure 1:
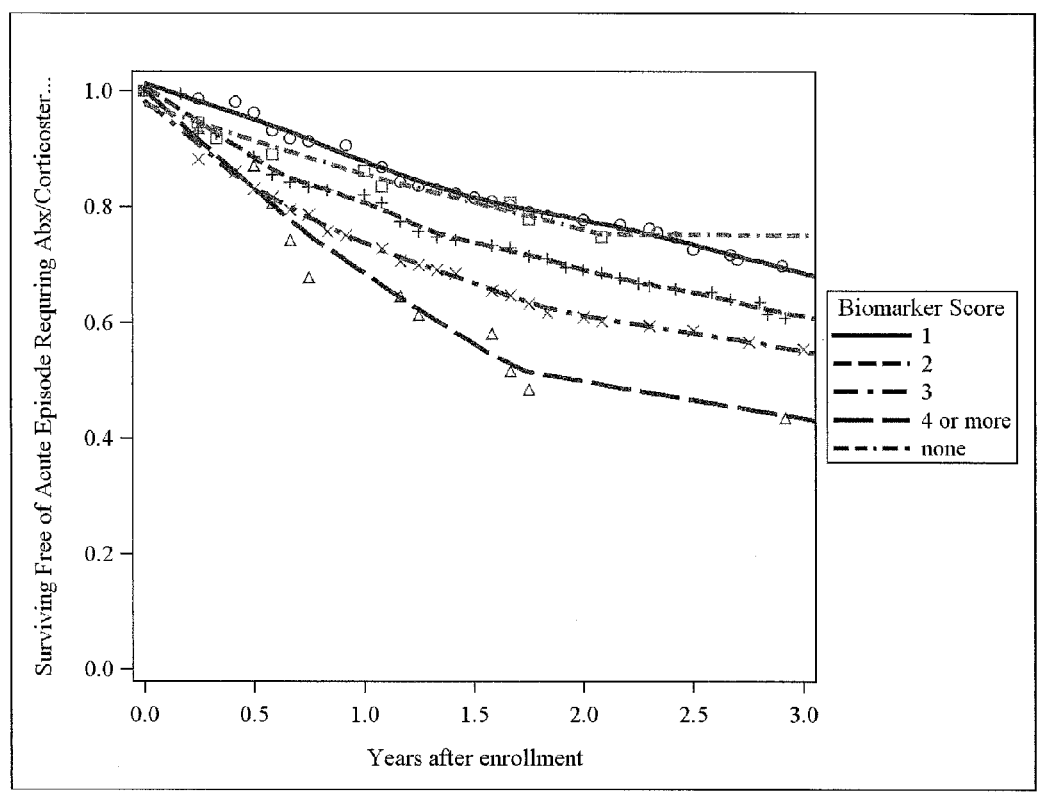
FIG. 1 shows risk of a moderate or severe exacerbation of COPD based on number of abnormal biomarkers.

One embodiment of the invention relates to a method of identifying a subject at risk for exacerbation of a respiratory disease comprising obtaining a biological sample from the subject; determining the expression level of at least one protein associated with the respiratory disease in the biological sample from the subject selected from CCL24, IL2RA, APOA4, GC, IgA, LPA, KLK3_F, FAS, NRCAM, TNFRSF10C, IL12B, IL23A and combinations thereof; and identifying the subject as at risk of exacerbation when the expression level of the at least one protein is altered as compared to the expression level of the least one protein from a control.

Another embodiment of the invention relates to a method to predict a subject's risk for exacerbation of a respiratory disease comprising obtaining a biological sample from the subject; analyzing the biological sample for at least one protein selected from CCL24, IL2RA, APOA4, GC, IgA, LPA, KLK3_F, FAS, NRCAM, TNFRSF10C, IL12B, IL23A and combinations thereof; wherein an altered expression level of the at least one protein compared to a control predicts the subject to be at risk for exacerbation for the respiratory disease.

Another embodiment of the invention relates to a method to treat a subject at risk for exacerbation of a respiratory disease comprising obtaining a biological sample from the subject; determining the expression level of at least one protein associated with the respiratory disease in the biological sample from the subject; wherein the at least one protein is selected from CCL24, IL2RA, APOA4, GC, IgA, LPA, KLK3_F, FAS, NRCAM, TNFRSF10C, IL12B, IL23A and combinations thereof; identifying the subject as at risk of exacerbation when the expression level of the at least one protein is altered as compared to a control; and treating the subject for the respiratory disease.

In any of the embodiments of the invention described herein, determining the expression level of the at least one protein associated with the respiratory disease comprises comparing the expression level of the at least one protein associated with the respiratory disease from the subject with the expression level of the at least one protein from a control. In one aspect, the expression level of the least one protein is considered altered if the expression level of the least one protein as compared to the expression level from the control is increased or decreased. In one aspect, analyzing the biological sample comprises determining the expression level of the at least one protein and comparing the expression level of the at least one protein from the subject with the expression level of the at least one protein from the control. In one aspect, the expression level of the least one protein is considered altered if the expression level of the least one protein as compared to the expression level from the control is increased or decreased.

In any of the embodiments of the invention described herein, the protein is selected from CCL24, IL2RA, APOA4, GC, IgA, LPA, KLK3_F, FAS, NRCAM, TNFRSF10C, IL12B, IL23A and combinations thereof. In one aspect the at least one protein is a protein selected from CCL24, IL2RA, APOA4, GC, IgA, LPA, KLK3_F and combinations thereof. In still another aspect, the at least one protein can be a protein selected from CCL24, IL2RA, FAS, NRCAM, TNFRSF10C, IL12B, IL23A and combinations thereof.

In one aspect, treating the subject at risk for exacerbation of a respiratory disease comprises administering to the subject a compound selected from a bronchodilator, a corticosteroid, an antibiotic, a phosphodiesaterease inhibitor and combinations thereof. In still another aspect, treating the subject at risk for exacerbation comprises hospitalization, pulmonary rehabilitation, oxygen therapy, surgery and/or lifestyle changes of the subject.

In any of the embodiments of the invention described herein, the respiratory disease can be chronic obstructive pulmonary disease (COPD).

Another embodiment relates to a kit for determining the expression level of at least one protein selected from CCL24, IL2RA, APOA4, GC, IgA, LPA, KLK3_F, FAS, NRCAM, TNFRSF10C, IL12B, and IL23A. In one aspect, the kit comprises a component selected from an antibody, an antisense RNA molecule, a molecular probe or tag and a microfluidics system, wherein in the component detects the expression level of the least one protein. In another aspect, the component detects the expression level of the at least one protein by a method selected from Western blot, immunoblot, enzyme-linked immunosorbant assay (ELISA), radioimmunoassay (RIA), immunoprecipitation, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), flow cytometry, protein binding assay and combinations thereof.

Yet another embodiment of the invention relates to a method of identifying a subject at risk of developing emphysema comprising obtaining a biological sample from the subject; determining the expression level of at least one protein associated with the respiratory disease in the biological sample from the subject selected from RAGE, CCL20, ICAM1, SERPINA7, CDH13, CDH1, and combinations thereof; and identifying the subject as at risk of developing emphysema when the expression level of the at least one protein is altered as compared to the expression level of the least one protein from a control.

Another embodiment of the invention relates to a method to predict a subject's risk for developing emphysema comprising obtaining a biological sample from the subject; analyzing the biological sample for at least one protein selected from RAGE, CCL20, ICAM1, SERPINA7, CDH13, CDH1, and combinations thereof; wherein an altered expression level of the at least one protein compared to a control predicts the subject to be at risk for developing emphysema. In one aspect, analyzing the biological sample comprises determining the expression level of the at least one protein and comparing the expression level of the at least one protein from the subject with the expression level of the at least one protein from a control, wherein the expression level of the least one protein is considered altered if the expression level of the least one protein as compared to the expression level from the control is increased or decreased.

Another embodiment of the invention relates to a method to treat a subject at risk for developing emphysema comprising obtaining a biological sample from the subject; determining the expression level of at least one protein in the biological sample from the subject selected from RAGE, CCL20, ICAM1, SERPINA7, CDH13, CDH1; identifying the subject as at risk of developing emphysema when the expression level of the at least one protein is altered as compared to a control; and treating the subject for emphysema.

In any of the embodiments of the invention described herein, determining the expression level of the at least one protein comprises comparing the expression level of the at least one protein selected from RAGE, CCL20, ICAM1, SERPINA7, CDH13, CDH1, and combinations thereof, from the subject with the expression level of the at least one protein from a control. In one aspect, the expression level of the least one protein is considered altered if the expression level of the least one protein as compared to the expression level from the control is increased or decreased.

In one aspect, treating the subject at risk for developing emphysema comprises administering to the subject a compound selected from a bronchodilator, a corticosteroid, an antibiotic, a phosphodiesterease inhibitor and combinations thereof. In still another aspect, treating the subject at risk for developing emphysema comprises hospitalization of the subject.

Another embodiment relates to a kit for determining the expression level of at least one protein selected from RAGE, CCL20, ICAM1, SERPINA7, CDH13, CDH1. In one aspect, the kit comprises a component selected from an antibody, an antisense RNA molecule, a molecular probe or tag and a microfluidics system, wherein in the component detects the expression level of the least one protein. In another aspect, the component detects the expression level of the at least one protein by a method selected from Western blot, immunoblot, enzyme-linked immunosorbant assay (ELISA), radioimmunoassay (RIA), immunoprecipitation, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), flow cytometry, protein binding assay and combinations thereof.

In any of the embodiments of the invention described herein, RAGE is soluble RAGE (sRAGE).

In any of the embodiments of the invention described herein, altered expression level of the at least one protein is at least about 5% different from the expression level of the control.

In any of the embodiments of the invention described herein, the biological sample is selected from blood, plasma, or peripheral blood mononuclear cells (PBMCs).

DETAILED DESCRIPTION OF THE INVENTION

This invention generally relates to systems, processes, methods, articles of manufacture, kits, and compositions that relate to respiratory disease treatments and diagnostics where the respiratory disease can include, but is not limited to chronic pulmonary disease (COPD), bronchitis, asthma and/or emphysema. The invention includes methods for identifying, predicting and/or treating a subject at risk of exacerbation of a respiratory disease such as COPD, as well as the presence or absence of emphysema. The inventors describe herein methods and uses of determining novel biomarkers and panels of biomarkers and demonstrate their use in determining if a subject is at risk of exacerbation of a respiratory disease as well as to determine the presence of a respiratory disease. The biomarkers of the present invention represent a novel, noninvasive tool to predict and/or identify subjects at risk of exacerbation of COPD as well as to predict and/or identify the presence or absence of emphysema in a subject. The presence and expression levels of systemic biomarkers, can be easily measured and can provide information regarding COPD and emphysema phenotypes, as well as providing significant value in diagnosing, managing and treating individuals with COPD exacerbation and/or emphysema. In addition a biomarker signature of COPD and/or emphysema phenotypes can provide insight to the pathogenesis of the diseases.

There is evidence for systemic manifestations in current and former smokers that result in comorbidities such as weight loss, depression, osteoporosis and cardiovascular disease that greatly contribute to poor health outcomes (Agusti, A., et al. Systemic inflammation and comorbidities in chronic obstructive pulmonary disease. *Proc Am Thorac Soc* 9, 43-46 (2012); Decramer, M., et al. Chronic obstructive pulmonary disease. *Lancet* 379, 1341-1351 (2012)). The pathophysiology of these systemic manifestations is unclear; however, recent work on peripheral blood biomarkers suggested that there may be biomarker signatures in blood that are associated with COPD phenotypes (Rosenberg, S. R., et al. Biomarkers in chronic obstructive pulmonary disease. *Transl Res* 159, 228-237 (2012)). Examples of candidate biomarkers previously reported in the literature include: C-reactive protein, interleukin 6, tumor necrosis factor α (TNFα), leptin and adiponectin (Thomsen, M., et al. Inflammatory Biomarkers and Comorbidities in Chronic Obstructive Pulmonary Disease. *Am J Respir Crit Care Med* (2012); Gaki, E., et al. Associations between BODE index and systemic inflammatory biomarkers in COPD. *Copd* 8, 408-413 (2011)).

Limitations of previous studies include small sample size and individual biomarkers. For example, in a study of 40 COPD patients, serum SP-D associated with increased exacerbations in a 6 month follow up period (Ozyurek, B.A., et al. Value of serum and induced sputum surfactant protein-D in chronic obstructive pulmonary disease. *Multidisciplinary respiratory medicine* 8, 36 (2013)). In a study of 145 COPD patients enrolled at baseline, 27 markers were measured in multiplex and baseline subjects were prospecitively followed for exacerbations for one year (Bafadhel, M., et al. Acute exacerbations of chronic obstructive pulmonary disease: identification of biologic clusters and their biomarkers. *Am J Respir Crit Care Med* 184, 662-671 (2011)). In this cohort, there were 189 moderate/severe subjects with N=21 hospitalized. There were no biomarkers predictive of future exacerbations per se; however sputum IL1β, serum CXC10 and peripheral eosinophilia were able to distinguish bacterial, viral, and eospinophilic subtypes of AECOPD. In 359 subjects from the ECLIPSE study (Evaluation of COPD Longitudinally to Identify Predictive Surrogate Endpoints—a non-interventional, observational, multicentre, three-year study in people with COPD), sputum neutrophilia was found not to be predictive of exacerbations (Singh, D., et al. Sputum neutrophils as a biomarker in COPD: findings from the ECLIPSE study. *Respir Res* 11, 77 (2010)). In 100 COPD patients, lower serum fetuin-A was associated with shorter onset to first exacerbation (Minas, M., et al. Fetuin-A is associated with disease severity and exacerbation frequency in patients with COPD. *COPD* 10, 28-34 (2013)). During hospitalization for AECOPD, high persistent levels of angiopoietin 2 converting enzyme were associated with poor prognosis (Nikolakopoulou, S., et al. Serum Angiopoietin-2 and CRP Levels During COPD Exacerbations. COPD (2013)). Serum CRP, serum amyloid A protein, and IL-6 have also been associated with poor prognosis of hospitalized patients (Gao, P., et al. Sputum inflammatory cell-based classification of patients with acute exacerbation of chronic obstructive pulmonary disease. *PLoS One* 8, e57678 (2013)). In 60 patients hospitalized for AECOPD, high hsCRP on admission was associated with poor outcome (Tofan, F., et al. High sensitive C-reactive protein for prediction of adverse outcome in acute exacerbation of chronic obstructive pulmonary disease. *Pneumologia* 61, 160-162 (2012)). Serum uric acid has also been associated with poor prognosis in 314 AECOPD patients admitted to the hospital (Bartziokas, K., et al. Serum uric acid on COPD exacerbation as predictor of mortality and future exacerbations. *Eur Respir J* (2013)). In 40 subjects with an acute exacerbation of COPD, SP-D was found to be elevated (Ju, C. R., et al. Serum surfactant protein D: biomarker of chronic obstructive pulmonary disease. *Dis Markers* 32, 281-287 (2012)). In 99 subjects admitted for AECOPD, high levels of n-terminal pro brian natriuretic peptide were associated with higher mortality rates (Hoiseth, A. D., et al. NT-proBNP independently predicts long term mortality after acute exacerbation of COPD—a prospective cohort study. *Respir Res* 13, 97 (2012)). In 20 admissions for AECOPD, serum and TNFα and IL-6 were elevated (Karadag, F., et al. Biomarkers of systemic inflammation in stable and exacerbation phases of COPD. *Lung* 186, 403-409 (2008)). In 73 subjects persistent elevated CRP was associated with higher admission rates to the hospital 50 days after discharge (Perera, W. R., et al. Inflammatory changes, recovery and recurrence at COPD exacerbation. *Eur Respir J* 29, 527-534 (2007)). In 41 subjects serum IL-6 and CRP levels were elevated during a COPD exacerbation (Hurst, J. R., et al. Systemic and upper and lower airway inflammation at exacerbation of chronic obstructive pulmonary disease. *Am J Respir Crit Care Med* 173, 71-78 (2006)). In 9 subjects, serum tissue inhibitors of metalloproteinase (TIMP)-1 concentrations were elevated during an AECOPD (Higashimoto, Y., et al. Increased serum concentrations of tissue inhibitor of metalloproteinase-1 in COPD patients. *Eur Respir J* 25, 885-890 (2005)). In 14 subjects admitted for an exacerbation, ICAM and IL-8 were elevated in serum (Gerritsen, W. B., et al. Markers of inflammation and oxidative stress in exacerbated chronic obstructive pulmonary disease patients. *Respir Med* 99, 84-90 (2005)). In 24 patients, vitamin A and E were lower during an exacerbation compared to baseline levels (Tug, T., et al. Antioxidant vitamins (A, C and E) and malondialdehyde levels in acute exacerbation and stable periods of patients with chronic obstructive pulmonary disease. *Clinical and investigative medicine. Medecine clinique et experimentale* 27, 123-128 (2004)). In 54 subjects IL-5 receptor α was elevated in serum during an exacerbation (Rohde, G., et al. Soluble interleukin-5 receptor alpha is increased in acute exacerbation of chronic obstructive pulmonary disease. *Int Arch Allergy Immunol* 135, 54-61 (2004)). In 100 subjects admitted for AECOPD, serum magnesium has been associated with readmission at one year (Bhatt, S. P., et al. Serum magnesium is an independent predictor of frequent readmissions due to acute exacerbation of chronic obstructive pulmonary disease. *Respir Med* 102, 999-1003 (2008)). Sputum neutrophila and inflammatory markers in patients hospitalized for AECOPD have worse outcomes (Gao, P., et al. Sputum inflammatory cell-based classification of patients with acute exacerbation of chronic obstructive pulmonary disease. *PLoS One* 8, e57678 (2013)). In a study of 145 COPD patients, sputum IL1β and eosinophilia at baseline were associated with future exacerbations (Bafadhel, M., et al. Acute exacerbations of chronic obstructive pulmonary disease: identification of biologic clusters and their biomarkers. *Am J Respir Crit Care Med* 184, 662-671 (2011)).

The inventors of the present invention have found novel, reliable and sensitive molecular markers which can be used to identify, predict and treat subjects who are susceptible to exacerbation of various respiratory diseases such as COPD. The inventors have also found novel, reliable and sensitive molecular markers which can be used to identify, predict and treat subjects predicted to have emphysema. For COPD, the biomarkers include CCL24 (chemokine ligand 24), IL2RA (Interleukin-2 receptor alpha chain), APOA4 (Apolipoprotein A-IV), GC (human group specific component (Gc)), IgA (immunoglobulin A), LPA (lipoprotein(a)), KLK3_F (a kallikrein protein), FAS (Fas cell surface death receptor), NRCAM (neuronal cell adhesion molecule), TNFRSF10C (tumor necrosis factor receptor superfamily, member 10c), IL12B (interleukin-12 subunit B), and IL23A (interleukin 23 subunit A) and combinations of these biomarkers.

One embodiment of the present invention relates to a method of indentifying a subject or predicting a subject at risk of exacerbation of a respiratory disease by determining the expression level of at least one protein associated with the respiratory disease. In one aspect the at least one protein is selected from CCL24, IL2RA, APOA4, GC, IgA, LPA, KLK3_F or combinations thereof. In still another aspect, the at least one protein is selected from CCL24, IL2RA, FAS, NRCAM, TNFRSF10C, IL12B, IL23A or combinations thereof. In still another aspect, the at least one protein associated with the respiratory disease is at least two, at least three, at least four, at least five, at least six proteins, at least seven, at least eight, at least nine, at least ten, at least eleven, or twelve of any combination of the proteins selected from CCL24, IL2RA, APOA4, GC, IgA, LPA, KLK3_F, FAS, NRCAM, TNFRSF10C, IL12B, and IL23A. The subject can be identified and/or predicted to be at risk of exacerbation of the respiratory disease when the expression level of the at least one protein is altered as compared to the expression level of the same protein from a control.

Another aspect of the present invention relates to a method to treat a subject at risk for exacerbation of a respiratory disease by determining the expression level of at least one protein associated with the respiratory disease in a biological sample from the subject, wherein the protein can be CCL24, IL2RA, APOA4, GC, IgA, LPA, KLK3_F, FAS, NRCAM, TNFRSF10C, IL12B, IL23A and combinations thereof. The subject can be identified as at risk of exacerbation of the respiratory disease when the expression level of the at least one protein is altered as compared to the expression level of the at least one protein from a control. Once the subject is identified as being at risk for exacerbation of the respiratory disease, the subject can be treated for the respiratory disease. In a preferred aspect, the respiratory disease is COPD.

Another embodiment of the present invention is a method of indentifying or predicting a subject at risk of developing emphysema by determining the expression level of at least one protein in a biological sample from the subject. In one aspect, the at least one protein is selected from RAGE (advanced glycosylation end-product receptor also referred to as AGER), CCL20 (macrophage inhibitory protein 3a), ICAM1 (intercellular adhesion molecule 1), SERPINA7 (serpin peptidase inhibitor, clade A (alpha-1 antiproteinase, antitrypsin member 7; thyroxin-binding globulin)), CDH13 (cadherin 13), CDH1 (cadherin 1) or combinations thereof. In still another aspect, the at least one protein is at least two, at least three, at least four, at least five or at least six proteins selected from RAGE, CCL20, ICAM1, SERPINA7, CDH13, and CDH1. The subject can be identified or predicted to be at risk of emphysema when the expression level of the at least one protein is altered as compared to the expression level of the same protein from a control. In a preferred aspect, the respiratory disease is COPD.

Another aspect of the present invention relates to a method to treat a subject at risk for emphysema by determining the expression level of at least one protein associated with the respiratory disease in a biological sample from the subject, wherein the protein is RAGE, CCL20, ICAM1, SERPINA7, CDH13, and CDH1 and combinations thereof. The subject can be identified as at risk of exacerbation of emphysema when the expression level of the at least one protein is altered as compared to the expression level of the same protein from a control. Once the subject is identified as being at risk for exacerbation of emphysema, the subject is treated for emphysema.

The subject can be identified and/or predicted as at risk of exacerbation of the respiratory disease, such as COPD and/or the presence of emphysema when the expression level of the at least one protein is altered. The expression level of the at least one protein can be determined to be altered by comparing the expression level of the at least one protein from the subject with the expression level of the at least one protein from a control. The expression level of the least one protein is considered altered if the expression level of the least one protein as compared to the expression level of the at least one protein from the control is increased or decreased. In one aspect, the expression levels of at least two, at least three, at least four, at least five, at least six, at least seven, at least eight, at least nine, at least ten, at least eleven or twelve of the proteins can increase, decrease or there can be a combination of expression levels, wherein one or more of the protein expression levels can be increased (or the genes are upregulated) as compared to the control expression level, while one or more different protein expression levels can be decreased (or the genes are downregulated) as compared to the control expression level. In one aspect, the altered expression level of the at least one protein is at least about 5%, at least about 10%, at least about 20%, at least about 30%, at least about 40%, at least about 50%, at least about 60%, at least about 70%, at least about 80%, at least about 90%, or 100% different (i.e. increased, decreased) from the expression level of the control.

As used herein, the term "expression", when used in connection with detecting the expression of a gene, can refer to detecting transcription of the gene (i.e., detecting mRNA levels) and/or to detecting translation of the gene (detecting the protein produced). To detect expression of a gene refers to the act of actively determining whether a gene is expressed or not. This can include determining whether the gene expression is upregulated as compared to a control, downregulated as compared to a control, or unchanged as compared to a control. Therefore, the step of detecting expression does not require that expression of the gene actually is upregulated or downregulated, but rather, can also include detecting that the expression of the gene has not changed (i.e., detecting no expression of the gene or no change in expression of the gene).

Expression of transcripts and/or proteins is measured by any of a variety of known methods in the art. For RNA expression, methods include but are not limited to: extraction of cellular mRNA and Northern blotting using labeled probes that hybridize to transcripts encoding all or part of the gene; amplification of mRNA using gene-specific primers, polymerase chain reaction (PCR), and reverse transcriptase-polymerase chain reaction (RT-PCR), followed by quantitative detection of the product by any of a variety of means; extraction of total RNA from the cells, which is then labeled and used to probe cDNAs or oligonucleotides encoding the gene on any of a variety of surfaces; in situ hybridization; and detection of a reporter gene.

Methods to measure protein expression levels generally include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry, as well as assays based on a property of the protein including but not limited to enzymatic activity or interaction with other protein partners. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al., 1993, *Anal. Biochem.* 212:457; Schuster et al., 1993, *Nature* 365:343). Other suitable assays for measuring the binding of one protein to another include, for example, immunoassays such as enzyme linked immunoabsorbent assays (ELISA) and radioimmunoassays (RIA); or determination of binding by monitoring the change in the spectroscopic or optical properties of the proteins through fluorescence, UV absorption, circular dichroism, or nuclear magnetic resonance (NMR). Many of these methods use a molecular probe or tag that labels antibodies, proteins, peptides, ligands and other biomolecules.

When comparing the expression level of the least one protein to the control expression level, it is to be understood that the expression level of the at least one protein is compared with the same protein from the control. For example, if the expression level of CCL24 and IL2RA are both determined or analyzed, then the expression level of CCL24 from the subject would be compared to the expression level of CCL24 from the control and likewise, the expression level of IL2RA from the subject would be compared to the expression level of IL2RA from the control.

As used herein, reference to a control, means a subject who is a relevant control to the subject being evaluated by the methods of the present invention. The control can be matched in one or more characteristics to the subject. More particularly, the control can be matched in one or more of the following characteristics, gender, age, smoking history and smoking status (smoker vs. non-smoker). In addition, the control is known not to have lung disease or if lung disease free. The control expression level used in the comparison of the methods of the present invention can be determined from one or more relevant control subjects.

The methods of the present invention can be used to predict, identify and/or treat subjects having a respiratory disease. In various aspects of the invention, the respiratory disease can be chronic obstructive pulmonary disease (COPD), bronchitis, asthma and/or emphysema A biological sample can include any bodily fluid or tissue from a subject that may contain the proteins contemplated herein, as well as the RNA and genes that encode the proteins. In some embodiments, the sample may comprise blood, plasma or peripheral blood mononuclear cells (PB-MCs), leukocytes, monocytes, lymphocytes, basophils or eosinophils. In a preferred aspect, the biological sample is peripheral blood mononuclear cells. In one aspect, the methods of the present invention can be performed on an ex vivo biological sample.

In other various aspects of the invention, the subject can be treated for exacerbation of the respiratory disease such as COPD and/or for treating emphysema by various methods including but not limited to smoking cessation, administration of a bronchodilator, an inhaled corticosteroid, administration of a phosphodiesterase inhibitor, administration of an antibiotic, administration of prednisone, increase in hospital stay, increase dose of antibiotics, pulmonary rehabilitation, oxygen therapy, surgery (bullectomy or lung volume reduction surgery), lifestyle changes (such as avoiding lung irritants) and combinations thereof, as well as, by known standard of care methods for the diseases. In one aspect, standard treatment methods such as those described above, are used in the treatment of subjects identified as at risk of exacerbation of COPD by the identification methods of the present invention. In one aspect, standard treatment methods such as those described above, are used in the treatment of subjects identified as having or predicted to have emphysema by the identification methods of the present invention.

In still other aspects of the invention, kits are considered. In some aspect, the kits can include an antibody, detection ability, and quantification ability. In still other aspects, the detection ability includes immunoflourescence. In one aspect, a kit is considered for indentifying a subject at risk of exacerbation of a respiratory disease comprising at least one antibody that specifically recognizes a protein selected from CCL24, IL2RA, APOA4, GC, IgA, LPA, KLK3_F, FAS, NRCAM, TNFRSF10C, IL12B, and IL23A, wherein recognition of the protein indicates the subject is at risk of exacerbation. In another aspect, a kit is for indentifying a subject at risk of exacerbation of a respiratory disease comprising at least one anti-sense RNA corresponding to a protein selected from the group consisting of CCL24, IL2RA, APOA4, GC, IgA, LPA, KLK3_F, FAS, NRCAM, TNFRSF10C, IL12B, and IL23A, wherein the presence of the protein indicates the subject is at risk of exacerbation. In still another aspect, a kit is for indentifying a subject at risk of exacerbation of a respiratory disease comprising a microfluidics system comprising one or more tags for identifying against a protein selected from CCL24, IL2RA, APOA4, GC, IgA, LPA, KLK3_F, FAS, NRCAM, TNFRSF10C, IL12B, and IL23A, wherein identification of the protein indicates the patient is at risk of exacerbation. In yet another aspect, a kit is for determining the expression level of at least one protein selected from CCL24, IL2RA, APOA4, GC, IgA, LPA, KLK3_F, FAS, NRCAM, TNFRSF10C, IL12B, and IL23A, wherein the kit comprises a component selected from an antibody, an antisense RNA molecule and a microfluidics system, wherein in the component detects the expression level of the least one protein. In still another aspect, a kit is for predicting a subject's risk of exacerbation of a respiratory disease comprising at least one antibody that specifically recognizes a protein selected from CCL24, IL2RA, APOA4, GC, IgA, LPA, KLK3_F, FAS, NRCAM, TNFRSF10C, IL12B, IL23A, wherein recognition of the protein predicts the subject is at risk of exacerbation. In another aspect, a kit is for predicting a subject's risk of exacerbation of a respiratory disease comprising at least one anti-sense RNA corresponding to a protein selected from CCL24, IL2RA, APOA4, GC, IgA, LPA, KLK3_F, FAS, NRCAM, TNFRSF10C, IL12B, IL23A, wherein the presence of the protein predicts the subject is at risk of exacerbation. In yet another aspect, a kit is for predicting a subject's risk of exacerbation of a respiratory disease comprising a microfluidics system comprising one or more tags for identifying against a protein selected from CCL24, IL2RA, APOA4, GC, IgA, LPA, KLK3_F, FAS, NRCAM, TNFRSF10C, IL12B, IL23A, wherein identification of the protein predicts the patient is at risk of exacerbation.

In a further aspect, a kit is considered for indentifying a subject at risk of developing emphysema comprising at least one antibody that specifically recognizes a protein selected from RAGE, CCL20, ICAM1, SERPINA7, CDH13,and CDH1, wherein recognition of the protein indicates the subject is at risk of developing emphysema. In still another aspect, a kit is for indentifying a subject at risk of developing emphysema comprising at least one anti-sense RNA corresponding to a protein selected from RAGE, CCL20, ICAM1, SERPINA7, CDH13, and CDH1, wherein the presence of the protein indicates the subject is at risk of developing a respiratory disease. In yet another aspect, a kit is for indentifying a subject at risk of developing emphysema comprising a microfluidics system comprising one or more tags for identifying against a protein selected from the group RAGE, CCL20, ICAM1, SERPINA7, CDH13, and CDH1, wherein identification of the protein indicates the patient is at risk of developing a respiratory disease. In another aspect, a kit is for predicting a subject's risk of developing emphysema comprising at least one antibody that specifically recognizes a protein selected from RAGE, CCL20, ICAM1, SERPINA7, CDH13, and CDH1, wherein recognition of the protein predicts the subject is at risk of developing emphysema. In yet another aspect, a kit for predicting a subject's risk of developing emphysema comprising at least one anti-sense RNA corresponding to a protein selected from the group consisting of RAGE, CCL20, ICAM1, SERPINA7, CDH13, and CDH1, wherein the presence of the protein predicts the subject is at risk of developing emphysema. In still another aspect, a kit is for predicting a subject's risk of developing a respiratory disease comprising a microfluidics system comprising one or more tags for identifying against a protein selected from RAGE, CCL20, ICAM1, SERPINA7, CDH13, and CDH1, wherein identification of the protein predicts the patient is at risk of developing emphysema.

COPD is a phenotypically heterogeneous disease, with the presence of emphysema having implications for risk stratification and management (Mohamed Hoesein F A., et al. Lung function decline in male heavy smokers relates to baseline airflow obstruction severity. *Chest. Dec* 2012;142 (6):1530-1538; Li Y, et al. Effect of emphysema on lung cancer risk in smokers: a computed tomography-based assessment. *Cancer Prev Res* (Phila). January 2011;4(1):43-50; de Torres J P., et al. Assessing the relationship between lung cancer risk and emphysema detected on low-dose CT of the chest. *Chest. December* 2007; 132(6):1932-1938; Rosenberg S R., et al. Biomarkers in chronic obstructive pulmonary disease. *Transl Res*. April 2012;159(4):228-237). The inventors have successfully identified and replicated a panel of peripheral blood biomarkers that was associated with emphysema independent of age, smoking status, body mass index, airflow limitation, and gender. These biomarkers (RAGE, ICAM1 and CCL20) were associated with emphysema regardless of quantification technique (LAA≤-950 and ≤-910 HU and LP15A) and were replicated in an independent COPD cohort (TESRA), thus strengthening their potential utility for defining clinically relevant emphysema.

The inventors' previous findings showed lower RAGE levels in peripheral blood as a biomarker of increased emphysema percentage in the lungs independent of gender, age, airflow limitation, body mass index and current smoking status. RAGE (advanced glycosylation end-product receptor also referred to as AGER) is an immunoglobulin family member that is highly expressed in human lung (Buckley S T., et al. The receptor for advanced glycation end products (RAGE) and the lung. *J Biomed Biotechnol.* 2010; 2010:917108). The RAGE pathway and soluble RAGE (sRAGE), a splice variant or proteolytic cleavage product of RAGE, have been associated with several inflammatory conditions such as diabetes mellitus, vascular disease and arthritis (Pullerits R., et al. Decreased levels of soluble receptor for advanced glycation end products in patients with rheumatoid arthritis indicating deficient inflammatory control. *Arthritis Res Ther.* 2005;7(4):R817-824; Falcone C., et al. Soluble RAGE plasma levels in patients with coronary artery disease and peripheral artery disease. *Scientific World Journal.* 2013;2013:584504). The sRAGE molecule binds damaged ligands preventing these from binding to cell surface receptors and activating cell signaling pathways (Alexiou P., et al. RAGE: a multi-ligand receptor unveiling novel insights in health and disease. *Curr Med Chem.* 2010;17(21):2232-2252). RAGE is active in damage-related conditions such as hyperglycemia, hypoxia, inflammation and oxidative stress (Uchida T., et al. Receptor for advanced glycation end-products is a marker of type I cell injury in acute lung injury. *Am J Respir Crit Care Med.* May 1, 2006;173(9):1008-1015). While fasting blood glucose measurements were not available, there was no association between RAGE levels and self-reported history of diabetes mellitus in the COPDGene study subjects. Lower levels of sRAGE have been described in individuals with airflow limitation (Smith D J., et al. Reduced soluble receptor for advanced glycation end-products in COPD. *Eur Respir J.* March 2011;37(3):516-522; Cockayne D A., et al. Systemic biomarkers of neutrophilic inflammation, tissue injury and repair in COPD patients with differing levels of disease severity. *PLoS One.* 2012;7(6):e38629. Other studies have found lower sRAGE levels associated with CT-assessed emphysema severity and cor pulmonale (Miniati M., et al. Soluble receptor for advanced glycation end products in COPD: relationship with emphysema and chronic cor pulmonale: a case-control study. *Respir Res.* 2011;12:37) and with CT-assessed emphysema and lower diffusing capacity of carbon monoxide using the TESRA (Treatment of Emphysema with a Selective Retinoid Agonist study) data described in this study in combination with the ECLIPSE investigators (Cheng D T., et al. Systemic soluble receptor for advanced glycation endproducts is a biomarker of emphysema and associated with AGER genetic variants in patients with chronic obstructive pulmonary disease. *Am J Respir Crit Care Med.* Oct. 15, 2013;188(8):948-957). Some studies suggest that sRAGE is increased in the lungs of patients with COPD and high levels of sRAGE may be associated with progression of emphysema (Wu L., et al. Advanced glycation end products and its receptor (RAGE) are increased in patients with COPD. *Respir Med.* March 2011;105(3):329-336). Interestingly, animal studies suggest RAGE/sRAGE plays a role in alveolar development and overexpression in mouse lung leads to the development of emphysema (Stogsdill M P., et al. Conditional overexpression of receptors for advanced glycation end-products in the adult murine lung causes airspace enlargement and induces inflammation. *Am J Respir Cell Mol Biol.* July 2013;49(1): 128-134). This suggests that sRAGE, by acting as a decoy molecule, may have a different role in the developing lung and the adult lung or low sRAGE levels in COPD may result in increased inflammatory signaling in the lung.

The inventors have found decreased ICAM1 levels correlate with increased severity of emphysema on CT scan, independent of smoking status, $FEV_1$ and other covariates. ICAM1 is expressed on vascular endothelial and immune cells and mediates cell transmigration and adhesion (Di Stefano A., et al. Upregulation of adhesion molecules in the bronchial mucosa of subjects with chronic obstructive bronchitis. *Am J Respir Crit Care Med.* March 1994;149(3 Pt 1):803-810). ICAM1 plays a role in the recruitment of inflammatory cells to the lung. There is currently limited information about the association of ICAM1 to COPD and emphysema. Higher serum levels of soluble ICAM1 have been demonstrated in COPD, where it correlated with the severity of airflow limitation, arterial hypoxemia and hypercarbia (El-Deek S E., et al. Surfactant protein D, soluble intercellular adhesion molecule-1 and high-sensitivity C-reactive protein as biomarkers of chronic obstructive pulmonary disease. *Med Princ Pract.* 2013;22(5):469-474; Huang H., et al. [Association of intercellular adhesion molecule-1 gene K469E polymorphism with chronic obstructive pulmonary disease]. *Zhong Nan Da Xue Xue Bao Yi Xue Ban.* January 2012;37(1):78-83). Other studies relate ICAM1 levels to active smoking (Lopez-Campos J L., et al. Increased levels of soluble ICAM-1 in chronic obstructive pulmonary disease and resistant smokers are related to active smoking *Biomark Med.* December 2012;6(6):805-811) and preliminary analysis from the MESA Lung Study (Multi-Ethnic Study of Atherosclerosis Lung Study) demonstrated that ICAM1 predicted 0.15%/year increase in CT-assessed emphysema, suggesting a role for this molecule as a biomarker of emphysema and that it may play a role in emphysema pathogenesis (Aaron C P., Schwartz, et al. Intercellular Adhesion Molecule (icam)1 And Longitudinal Change In Percent Emphysema And Lung Function: The MESA Lung Study. *Am J Rspir Crit Care Med.* 2013;187: A1523).

CCL20 or macrophage inhibitory protein 3a, a chemokine receptor ligand, is involved in the recruitment of inflammatory cells through chemokine receptor 6 (CCR6), its only known receptor (Dieu-Nosjean M C., et al. Macrophage inflammatory protein 3alpha is expressed at inflamed epithelial surfaces and is the most potent chemokine known in attracting Langerhans cell precursors. *J Exp Med.* Sep. 4, 2000;192(5):705-718). In both the COPDGene study and the TESRA study, CCL20 levels were inversely and significantly associated with emphysema although methodological considerations prevented a meta-analysis. Lower CCL20 levels have been described in broncho-alveolar lavage fluid of smokers (Meuronen A., et al. Decreased cytokine and chemokine mRNA expression in bronchoalveolar lavage in asymptomatic smoking subjects. *Respiration.* 2008;75(4): 450-458). The CCR6/CCL20 complex is one of the most potent regulators of dendritic cell migration to the lung and CCR6 knockout mice may be partially protected against cigarette smoke-induced emphysema due to reduced recruitment of inflammatory cells to the lung (Bracke K R., et al. Cigarette smoke-induced pulmonary inflammation and emphysema are attenuated in CCR6-deficient mice. *J Immunol.* Oct. 1, 2006;177(7):4350-4359). These data suggest that increased activity of the CCL20/CCR6 pathway may increase the susceptibility to emphysema.

CDH1 was negatively correlated with radiologic emphysema across all emphysema outcome measurements. CDH1 or E cadherin is an epithelial cell adhesion molecule that regulates cell differentiation and morphogenesis, and is associated with lung fibrosis and cancer (Gall T M., et al. Gene of the month: E-cadherin (CDH1). *J Clin Pathol,* November 2013;66(11):928-932). CDH1 may be a marker of epithelial cell injury and epithelial to mesenchymal transition that is believed to play a role in small airway remodeling in COPD (Milara J., et al. Epithelial to mesenchymal transition is increased in patients with COPD and induced by cigarette smoke. *Thorax.* May 2013;68(5):410-420). Genetic polymorphisms in CDH1 have been associated with development of COPD and decline in lung function (Tsuduki K N H., et al. Genetic polymorphism of e-cadherin and copd. *Am J Respir Crit Care Med.* 2009; 179:A2999). CDH13 or H cadherin is another adhesion molecule that may influence surfactant protein D levels and serum adiponectin levels, both implicated in the pathogenesis of COPD; however, CDH13 itself has not been associated with quantitative emphysema to date (Kasahara D I., et al. Role of the adiponectin binding protein, t-cadherin (cdh13), in pulmonary responses to sub-acute ozone. *PLoS One.* 2013;8:e65829; Takeuchi T., et al. T-cadherin (cdh13, h-cadherin) expression downregulated surfactant protein d in bronchioloalveolar cells. *Virchows Archiv: and international journal of pathology.* 2001;438:370-375). The inventors have found higher levels of CDH13 to be associated with CT-assessed emphysema in the COPDGene cohort, but these were not available for validation in the TESRA cohort. Higher SERPINA7 levels were also associated with more radiologic emphysema. SERPINA7 does not have protease inhibitor capabilities and is also known as thyroid binding globulin. The inventor's findings represent a new association for SERPINA7 with COPD.

As demonstrated in the examples presented herein, peripheral blood biomarkers correlate with the severity and distribution of emphysema and the unique association of some biomarkers with upper zone emphysema can provide insight to the pathogenesis of this particular phenotype of COPD and have therapeutic benefits.

As further demonstrated in the examples below, a peripheral blood biomarker signature of emphysema, independent of other clinical variables, in current and former smokers with normal lung function and with COPD is shown. As discussed below, 115 candidate biomarkers were measured in peripheral blood of 602 individuals enrolled in the COPDGene multi-centered study. Predictive statistical modeling was used to determine their associations with quantitative emphysema measurements on HRCT scans independent of covariates such as age, gender, race, body mass index, active smoking status and airflow limitation. Different biomarker signatures associated with upper lung and lower lung emphysema distributions as a means of phenotyping COPD were also evaluated.

The following examples are provided for illustrative purposes, and are not intended to limit the scope of the invention as claimed herein. Any variations which occur to the skilled artisan are intended to fall within the scope of the present invention. All references cited in the present application are incorporated by reference herein to the extent that there is no inconsistency with the present disclosure.

EXAMPLES

Example 1

Study Population

Study participants provided written informed consent. At the time of enrollment, all subjects were 45-80 years old, had a history of smoking at least 10 pack-years, and had not had an acute respiratory exacerbation for at least 30 days prior to enrollment. 1958 of these subjects from 5 clinical centers participated in an ancillary study in which they provided baseline fresh frozen plasma collected using a p100 tube (BD) (Carolan, B. J., et al. The association of adiponectin with computed tomography phenotypes in chronic obstructive pulmonary disease. *Am J Respir Crit Care Med* 188, 561-566 (2013)); 1350 of these subjects met all of the following criteria: they were from two sites, were non-Hispanic White (NHW) and actively participated in a longitudinal follow up study (describe in Regan E. A., et al. Genetic epidemiology of COPD (COPDGene) study design. *COPD* 7, 32-43 (2010)). From this group, 602 subjects with and without COPD were matched for gender and smoking status and selected for a comprehensive biomarker study.

Biomarker Panel and Data Generation 115 candidate biomarkers were selected from the literature. A custom 15 panel assay for these biomarkers was created using Myriad-RBM (Austin, Tex.) multiplex technology (see Table 1).

TABLE 1

Biomarkers studied

| VarName | RBM_Name | Percent Below | Percent QNS | Mean | Median | SD |
|---|---|---|---|---|---|---|
| A2M | Alpha-2-Macroglobulin (A2Macro) | 0% | 0% | 1.07 | 1.00 | 0.19 |
| ADIPOQ | Adiponectin | 0% | 0% | 6.81 | 5.30 | 5.50 |
| APCS | Serum Amyloid P-Component (SAP) | 0% | 0% | 17.72 | 17.00 | 5.11 |
| APOA4 | Apolipoprotein A-IV (Apo A-IV) | 0% | 0% | 315.72 | 167.00 | 375.39 |
| AXL | AXL Receptor Tyrosine Kinase (AXL) | 0% | 0% | 12.48 | 12.00 | 4.32 |
| B2M | Beta-2-Microglobulin (B2M) | 0% | 0% | 1.88 | 1.80 | 0.74 |
| C3 | Complement C3 (C3) | 0% | 0% | 1.23 | 1.20 | 0.26 |
| CCL16 | Chemokine CC-4 (HCC-4) | 0% | 0% | 5.67 | 5.30 | 2.50 |
| CCL18 | Pulmonary and Activation-Regulated Chemokine (PARC) | 0% | 0% | 96.47 | 89.00 | 51.94 |
| CCL22 | Macrophage-Derived Chemokine (MDC) | 0% | 0.17% | 414.97 | 400.00 | 153.72 |
| CCL23 | Myeloid Progenitor Inhibitory Factor 1 (MPIF-1) | 0% | 0% | 1.47 | 1.40 | 0.66 |
| CCL24 | Eotaxin-2 | 0% | 0.17% | 692.59 | 553.00 | 488.04 |
| CCL4 | Macrophage Inflammatory Protein-1 beta (MIP-1 beta) | 0% | 0.17% | 270.36 | 197.00 | 567.59 |
| CCL5 | T-Cell-Specific Protein RANTES (RANTES) | 0% | 0% | 12.71 | 9.80 | 10.32 |
| CDH1 | Cadherin-1 (E-Cad) | 0% | 0% | 3478.57 | 3110.00 | 1621.58 |
| CDH13 | Cadherin-13 (T-cad) | 0% | 0.17% | 19.12 | 18.00 | 5.61 |

TABLE 1-continued

| | Biomarkers studied | | | | | |
|---|---|---|---|---|---|---|
| VarName | RBM_Name | Percent Below | Percent QNS | Mean | Median | SD |
| CEACAM1 | Carcinoembryonic antigen-related cell adhesion molecule 1 (CEACAM1) | 0% | 0.17% | 14.15 | 14.00 | 4.11 |
| CHGA | Chromogranin-A (CgA) | 0% | 0.17% | 1227.51 | 485.50 | 2525.81 |
| CRP | C-Reactive Protein (CRP) | 0% | 0% | 5.15 | 2.70 | 8.02 |
| CSTB | Cystatin-B | 0% | 0% | 10.33 | 9.40 | 4.80 |
| CXCL10 | Interferon gamma Induced Protein 10 (IP-10) | 0% | 0% | 318.76 | 262.00 | 211.47 |
| CXCL9 | Monokine Induced by Gamma Interferon (MIG) | 0% | 0% | 1371.49 | 1020.00 | 1362.88 |
| DCN | Decorin | 0% | 0.17% | 2.00 | 1.90 | 0.46 |
| F7 | Factor VII | 0% | 0.33% | 580.69 | 563.00 | 195.11 |
| FTL_FTH1 | Ferritin (FRTN) | 0% | 0% | 170.21 | 120.00 | 169.73 |
| GC | Vitamin D-Binding Protein (VDBP) | 0% | 0% | 277.05 | 278.00 | 97.48 |
| ICAM1 | Intercellular Adhesion Molecule 1 (ICAM-1) | 0% | 0.33% | 134.63 | 125.00 | 47.81 |
| IgM | Immunoglobulin M (IgM) | 0% | 0% | 1.88 | 1.60 | 1.45 |
| IL16 | Interleukin-16 (IL-16) | 0% | 0.17% | 408.68 | 393.00 | 167.55 |
| IL18BP | Interleukin-18-binding protein (IL-18bp) | 0% | 0.17% | 12.47 | 11.00 | 5.47 |
| IL2RA | Interleukin-2 receptor alpha (IL-2 receptor alpha) | 0% | 0.17% | 2360.53 | 2100.00 | 1251.39 |
| IL6R | Interleukin-6 receptor (IL-6r) | 0% | 0% | 28.68 | 28.00 | 7.77 |
| KIT | Mast/stem cell growth factor receptor (SCFR) | 0% | 0% | 8.23 | 8.10 | 2.02 |
| MB | Myoglobin | 0% | 0% | 41.71 | 34.00 | 32.88 |
| MMP3 | Matrix Metalloproteinase-3 (MMP-3) | 0% | 0.33% | 10.01 | 8.20 | 6.83 |
| PECAM1 | Platelet endothelial cell adhesion molecule (PECAM-1) | 0% | 0.17% | 45.57 | 44.00 | 11.76 |
| SELE | E-Selectin | 0% | 0% | 8.47 | 7.60 | 4.35 |
| SERPINA1 | Alpha-1-Antitrypsin (AAT) | 0% | 0% | 1.85 | 1.80 | 0.41 |
| SERPINA7 | Thyroxine-Binding Globulin (TBG) | 0% | 0% | 37.40 | 37.00 | 8.84 |
| SFTPD | Pulmonary surfactant-associated protein D (SP-D) | 0% | 0.17% | 7.35 | 6.60 | 3.84 |
| SHBG | Sex Hormone-Binding Globulin (SHBG) | 0% | 0% | 63.31 | 54.00 | 37.31 |
| SLPI | Antileukoproteinase (ALP) | 0% | 0% | 37.99 | 37.00 | 8.02 |
| SOD1 | Superoxide Dismutase 1, soluble (SOD-1) | 0% | 0% | 34.81 | 32.00 | 15.48 |
| SORT1 | Sortilin | 0% | 0% | 6.07 | 5.80 | 1.80 |
| SPINK1 | Pancreatic secretory trypsin inhibitor (TATI) | 0% | 0% | 15.24 | 13.00 | 8.80 |
| TGFB1_LAP | Latency-Associated Peptide of Transforming Growth Factor beta 1 (LAP TGF-b1) | 0% | 0.17% | 4.59 | 3.80 | 3.02 |
| THBD | Thrombomodulin (TM) | 0% | 0% | 4.60 | 4.40 | 1.26 |
| TIMP1 | Tissue Inhibitor of Metalloproteinases 1 (TIMP-1) | 0% | 0% | 76.36 | 72.00 | 20.72 |
| TIMP2 | Tissue Inhibitor of Metalloproteinases 2 (TIMP-2) | 0% | 0% | 66.98 | 66.00 | 11.65 |
| TNFRSF10C | TNF-Related Apoptosis-Inducing Ligand Receptor 3 (TRAIL-R3) | 0% | 0% | 13.66 | 13.00 | 7.45 |
| TNFRSF11B | Osteoprotegerin (OPG) | 0% | 0.17% | 5.69 | 5.50 | 1.66 |
| TNFRSF1A | Tumor Necrosis Factor Receptor I (TNF RI) | 0% | 0.17% | 1740.53 | 1630.00 | 694.70 |

TABLE 1-continued

| | Biomarkers studied | | | | | |
|---|---|---|---|---|---|---|
| VarName | RBM_Name | Percent Below | Percent QNS | Mean | Median | SD |
| TNFRSF1B | Tumor necrosis factor receptor 2 (TNFR2) | 0% | 0% | 6.19 | 5.60 | 2.43 |
| VCAM1 | Vascular Cell Adhesion Molecule-1 (VCAM-1) | 0% | 0% | 536.37 | 505.00 | 183.46 |
| FGA_FGB_FGG | Fibrinogen | 0.17% | 0% | 4.28 | 4.20 | 1.09 |
| IL18 | Interleukin-18 (IL-18) | 0.17% | 0.17% | 259.54 | 229.00 | 157.76 |
| LPA | Apolipoprotein(a) (Lp(a)) | 0.17% | 0% | 8.05 | 7.85 | 1.97 |
| MMP9 | Matrix Metalloproteinase-9 (MMP-9) | 0.17% | 0.33% | 373.31 | 299.50 | 265.66 |
| NPPB_PH | N-terminal prohormone of brain natriuretic peptide (NT proBNP) | 0.17% | 0% | 721.40 | 460.50 | 903.87 |
| NRCAM | Neuronal Cell Adhesion Molecule (Nr-CAM) | 0.17% | 0% | 1.02 | 0.90 | 0.73 |
| SERPINA3 | Alpha-1-Antichymotrypsin (AACT) | 0.17% | 0% | 788.58 | 749.00 | 371.21 |
| CCL2 | Monocyte Chemotactic Protein 1 (MCP-1) | 0.33% | 0.17% | 151.00 | 139.00 | 59.99 |
| CCL8 | Monocyte Chemotactic Protein 2 (MCP-2) | 0.33% | 0% | 30.30 | 27.00 | 23.76 |
| IgA | Immunoglobulin A (IgA) | 0.33% | 0% | 2.32 | 2.00 | 1.36 |
| ANGPT1 | Angiopoietin-1 (ANG-1) | 0.50% | 0.17% | 7.76 | 7.00 | 3.38 |
| BDNF | Brain-Derived Neurotrophic Factor (BDNF) | 0.50% | 0.33% | 4.21 | 3.00 | 3.93 |
| CKM_CKB | Creatine Kinase-MB (CK-MB) | 0.50% | 0.17% | 1.81 | 1.40 | 1.41 |
| MDK | Midkine | 0.66% | 0.17% | 2.16 | 2.00 | 1.04 |
| KITLG | Stem Cell Factor (SCF) | 0.83% | 0.33% | 313.34 | 302.00 | 102.99 |
| SERPINE1 | Plasminogen Activator Inhibitor 1 (PAI-1) | 0.83% | 0% | 38.57 | 34.00 | 23.99 |
| CXCL5 | Epithelial-Derived Neutrophil-Activating Protein 78 (ENA-78) | 1.00% | 0.17% | 0.95 | 0.70 | 0.90 |
| VWF | von Willebrand Factor (vWF) | 1.16% | 0% | 84.05 | 77.00 | 41.75 |
| AGER | Receptor for advanced glycosylation end products (RAGE) | 1.33% | 0% | 2.75 | 2.30 | 2.03 |
| HGF | Hepatocyte Growth Factor (HGF) | 1.33% | 0% | 5.79 | 5.60 | 2.56 |
| IL8 | Interleukin-8 (IL-8) | 1.33% | 0.17% | 10.73 | 9.40 | 6.10 |
| VEGFA | Vascular Endothelial Growth Factor (VEGF) | 1.33% | 0.33% | 128.23 | 116.00 | 59.23 |
| HP | Haptoglobin | 1.49% | 0% | 1.60 | 1.40 | 0.92 |
| CCL13 | Monocyte Chemotactic Protein 4 (MCP-4) | 2.65% | 0% | 1913.71 | 1650.00 | 1340.28 |
| FAS | FASLG Receptor (FAS) | 3.48% | 0% | 18.44 | 15.00 | 23.54 |
| LTF | Lactoferrin (LTF) | 4.15% | 0% | 16.40 | 14.00 | 9.80 |
| IFNG | Interferon gamma (IFN-gamma) | 8.62% | 0.17% | 3.81 | 3.40 | 2.28 |
| CA9 | Carbonic anhydrase 9 (CA-9) | 43.28% | 0.17% | 0.52 | 0.49 | 0.25 |
| CCL11 | Eotaxin-1 | 56.38% | 0.33% | 199.75 | 180.00 | 62.97 |
| CCL20 | Macrophage Inflammatory Protein-3 alpha (MIP-3 alpha) | 73.13% | 0% | 84.83 | 50.00 | 149.04 |
| CCL3 | Macrophage Inflammatory Protein-1 alpha (MIP-1 alpha) | 84.74% | 0.17% | 67.19 | 47.00 | 71.88 |
| IgE | Immunoglobulin E (IgE) | 43.62% | 0.17% | 166.89 | 57.00 | 369.27 |
| IL10 | Interleukin-10 (IL-10) | 90.55% | 0.17% | 14.78 | 8.90 | 27.31 |
| IL12B | Interleukin-12 Subunit p40 (IL-12p40) | 38.31% | 0.33% | 0.30 | 0.27 | 0.08 |
| IL15 | Interleukin-15 (IL-15) | 58.37% | 0.33% | 0.62 | 0.55 | 0.23 |
| IL17A | Interleukin-17 (IL-17) | 94.03% | 0.33% | 26.33 | 3.60 | 132.29 |
| IL1RN | Interleukin-1 receptor antagonist (IL-1ra) | 76.62% | 0.33% | 300.85 | 255.00 | 181.14 |
| IL23A | Interleukin-23 (IL-23) | 75.95% | 0.33% | 0.88 | 0.82 | 0.18 |
| INS_intact | Proinsulin, Intact | 83.75% | 0% | 23.20 | 17.00 | 18.61 |
| INS_total | Proinsulin, Total | 83.75% | 0% | 98.70 | 68.00 | 76.12 |

TABLE 1-continued

Biomarkers studied

| VarName | RBM_Name | Percent Below | Percent QNS | Mean | Median | SD |
|---|---|---|---|---|---|---|
| KLK3_F | Prostate-Specific Antigen, Free (PSA-f) | 49.75% | 0.17% | 0.21 | 0.16 | 0.17 |
| MDA_LDL | Malondialdehyde-Modified Low-Density Lipoprotein (MDA-LDL) | 82.42% | 0% | 36.10 | 32.00 | 14.59 |
| MICA | MHC class I chain-related protein A (MICA) | 45.94% | 0.17% | 144.94 | 124.00 | 77.31 |
| OLR1 | Lectin-Like Oxidized LDL Receptor 1 (LOX-1) | 94.53% | 0% | 1.35 | 0.90 | 1.20 |
| IL1A | Interleukin-1 alpha (IL-1 alpha) | 95.52% | 0.33% | 0.00 | 0.00 | 0.00 |
| TNF | Tumor Necrosis Factor alpha (TNF-alpha) | 97.68% | 0.17% | 53.54 | 33.00 | 42.80 |
| IL6 | Interleukin-6 (IL-6) | 98.18% | 0.17% | 87.80 | 24.00 | 152.06 |
| HSPD1 | Heat Shock Protein 60 (HSP-60) | 98.34% | 0% | 105.40 | 106.00 | 40.94 |
| LTA | Tumor Necrosis Factor beta (TNF-beta) | 98.51% | 0.17% | 35.63 | 29.00 | 25.01 |
| IL1B | Interleukin-1 beta (IL-1 beta) | 98.67% | 0.33% | 5.67 | 5.65 | 0.78 |
| IL2 | Interleukin-2 (IL-2) | 98.84% | 0.17% | 20.02 | 9.75 | 25.48 |
| IL7 | Interleukin-7 (IL-7) | 98.84% | 0.17% | 17.82 | 11.00 | 16.39 |
| IL13 | Interleukin-13 (IL-13) | 99.17% | 0.17% | 7.68 | 6.70 | 2.22 |
| IL12A_IL12B | Interleukin-12 Subunit p70 (IL-12p70) | 99.34% | 0.33% | 68.50 | 68.50 | 23.33 |
| IL4 | Interleukin-4 (IL-4) | 99.34% | 0.17% | 65.00 | 48.00 | 44.03 |
| CSF2 | Granulocyte-Macrophage Colony-Stimulating Factor (GM-CSF) | 99.67% | 0.17% | 832.00 | 832.00 | NA |
| IL3 | Interleukin-3 (IL-3) | 99.83% | 0.17% | NaN | NA | NA |
| IL5 | Interleukin-5 (IL-5) | 99.83% | 0.17% | NaN | NA | NA |
| NGF | Nerve Growth Factor beta (NGF-beta) | 100% | 0% | NaN | NA | NA |
| S100B | S100 calcium-binding protein B (S100-B) | 100% | 0% | NaN | NA | NA |

Clinical Data and Definitions

Full details about COPDGene study and the collection of clinical data has been described previously (Regan E. A., et al. Genetic epidemiology of COPD (COPDGene) study design. *COPD* 7, 32-43 (2010)). COPD was defined as post bronchodilator ratio of forced expiratory volume in one second ($FEV_1$) to forced expiratory volume (FVC)<0.70. COPD was further classified 1-4 based on Global Initiative for Chronic Obstructive Lung Disease (GOLD) guidelines (Fabbri, L. M., et al. Global Strategy for the Diagnosis, Management and Prevention of COPD: 2003 update Eur Respir J 22, 1-2). Current or ex-smokers at risk for COPD but without spirometric evidence of airflow obstruction ($FEV_1/FVC \geq 0.70$) were classified as controls (formerly GOLD 0). Subjects with $FEV_1/FVC \geq 0.70$ and $FEV_1 < 80\%$ were considered unclassified (GOLD U) (30). Emphysema was quantified by the percent of lung voxels <-950 Hounsfield Units (HU) on the inspiratory images of CT scan. Gas trapping was quantified by the percent of lung voxels <-856 HU on the expiratory images. Respiratory health questionnaires included: Medical Research Council (MRC) dyspnea score, (SF-36), and St. George's Respiratory Questionnaire (SGRQ).

Acute episode of respiratory disease were ascertained on LFU by asking "Since we last spoke, have you had an episode of increased cough and phlegm or shortness of breath, which lasted 48 hours or more?" If answered yes, subjects were further asked whether they received antibiotics or corticosteroids. Additional questions asked at each LFU contact included whether the subject urgently visited his/her doctor's office, went to an emergency room, or was hospitalized. Subjects were considered to have experienced a moderate episode if they answered yes to either antibiotic or corticosteroid use. A severe episode was a report of hospitalization for an acute episode of respiratory disease. The total number of episodes was defined as the sum during each 6-month follow-up period. The time to an episode was determined using the date at which an episode was first reported.

Statistical Analysis

Unless otherwise specified, analyses were conducted using SASversion 9.3 (SAS Institute, Cary, N.C.) or R version 2.14 (R Development Core Team, Vienna Austria). Colinnearity among biomarkers was assessed using Pearson correlation. Biomarkers with more than 10% and less than 95% of values below the lower limit of quantitation (LLOQ) were transformed into binary variables (above or below LLOQ). Biomarkers with greater than 95% values below LLOQ were excluded from analysis. For all other biomarkers an empirical normal quantile transformation projecting the ranks onto an inverse normal distribution (Singh D., et al. Sputum neutrophils as a biomarker in COPD: findings from the ECLIPSE study. *Respir Res* 11, 77 (2010)). Episodes in the year prior to enrollment and during longitudinal follow up were modeled with negative binomial regression with offset for exposure time and a zero inflation model to account for the excess number of subjects who reported no acute episodes of respiratory disease. Cox proportional hazards multiple regression was used to determine hazard ratios for time to first episode. The stepwise multiple regression models variable selection method used an entry probability <0.15 and exit probability of >0.05.

Results

Study Population

Demographics, physiology, health scores, quantitative CT measurements and medication use by COPD status are listed in Table 2. There were differences between controls and individuals with COPD with respect to age at enrollment and pack-year history of smoking (p<0.001) with older age and higher pack-years in the COPD group. With regard to gender and smoking status, there were no statistically significant differences in distribution between the control group and COPD group (p>0.05). Body mass index (BMI) was lower in the COPD subjects (p=0.016). Emphysema, oxygen use, airway wall measurements, and health assessment scores (MRC, SF-36, and SGRQ) were significantly worse for subjects with COPD (P<0.001).

TABLE 2

Subject Characteristics (N = 602)

| | Control (N = 249) | COPD (N = 353) | P Value |
|---|---|---|---|
| Age (yr) | 61 ± 8 | 65 ± 8 | <0.001 |
| Female gender (%) | 50 | 52 | N.S. |
| Current smoker (%) | 27 | 23 | N.S. |
| Smoking History (pack-years) | 38 ± 23 | 54 ± 27 | <0.001 |
| Chronic Bronchitis (%) | 10 | 25 | <0.001 |
| GERD (%) | 30 | 35 | N.S. |
| Physiology | | | |
| Body-mass index (kg/m$^2$) | 29 ± 5 | 28 ± 6 | 0.016 |
| FEV$_1$ post bronchodilator (liters) | 2.94 ± 0.71 | 1.34 ± 0.63 | <0.001 |
| FEV$_1$ post bronchodilator (% predicted) | 98 ± 11 | 47 ± 18 | |
| FEV$_1$/FVC post bronchodilator | 0.78 ± 0.05 | 0.45 ± 0.14 | |
| Change in FEV$_1$ pre- and post-bronchodilator (%) | 4.4 ± 5.0 | 9.4 ± 11.8 | <0.001 |
| Distance walked in 6 min (m) | 506 ± 93 | 291 ± 107 | <0.001 |
| BODE index | 0.3 ± 0.7 | 2.9 ± 2.0 | <0.001 |
| Using oxygen on enrollment (%) | 3 | 52 | <0.001 |
| HRCT measurements | | | |
| Emphysema | 2 ± 3 | 15 ± 13 | <0.001 |
| Gas Trapping | 9 ± 7 | 42 ± 21 | <0.001 |
| Pi10 | 3.60 ± 0.10 | 3.70 ± 0.13 | <0.001 |
| WA % | 59.2 ± 2.6 | 62.4 ± 2.8 | <0.001 |
| Patient-reported outcomes | | | |
| MRC dyspnea score | 0.5 ± 1.0 | 2.2 ± 1.4 | <0.001 |
| SF-36 General Health* | 71 ± 22 | 52 ± 24 | <0.001 |
| SGRQ | 12 ± 15 | 39 ± 21 | <0.001 |

TABLE 2-continued

Subject Characteristics (N = 602)

| | Control (N = 249) | COPD (N = 353) | P Value |
|---|---|---|---|
| Exacerbations 12 months prior to entry | | | |
| Moderate and severe | 0.16 ± 0.60 | 0.92 ± 1.37 | <0.001 |
| Severe (hospitalized) | 0.03 ± 0.17 | 0.25 ± 0.43 | <0.001 |
| Exacerbations during longitudinal follow up | | | |
| Years followed | 3.1 ± 0.8 | 3.1 ± 0.9 | N.S. |
| Moderate and severe (#/year) | 0.24 ± 0.71 | 1.02 ± 1.74 | <0.001 |
| Severe hospitalized (#/year) | 0.04 ± 0.24 | 0.32 ± 0.91 | <0.001 |

GOLD 0: (FEV$_1$/FVC >0.7 and FEV$_1$ % >80).;
GOLD 1 (FEV$_1$/FVC >0.7 and FEV$_1$ % <80)
Lung attenuation area (LAA);
Hounsfield Units (HU);
forced expiratory volume at one second (FEV$_1$);
forced vital capacity (FVC);
long-acting β-agonist bronchodilator (LABA);
inhaled corticosteroid (ICS);
Emphysema (LAA % <−950 HU) on inspiration;
Gas Trapping (LAA % <−856) on expiration;
Pi10 (square root of wall area percent for 10 μum airway;
WA % (segmental wall area %);
Medical Research Council (MRC);
*Short Form Health Survey (SF-36): only 47% of cohort had this measurement;
St. George's Respiratory Questionnaire (SGRC);
means ± standard deviations are shown for continuous measures whereas dichotomous variables are shown as %.;
P values represent probability that GOLD group variable means are the same.

Biomarker Panel

Of the 115 biomarkers listed in Table 1, 82 had at least 92% of values above the lower limit of quantitation (LLOQ); these biomarkers were transformed using an empirical normal quantile transformation. 16 biomarkers were excluded from analysis because more than 95% of values were below LLOQ. The remaining 17 biomarkers were transformed into a binary variables (above or below LLOQ). Two biomarkers (intact and total insulin) were highly correlated (p=XX). Thus total insulin was removed from the analysis.

Plasma Biomarkers Associated with Exacerbations Prior to Enrollment

In the 12 months preceding enrollment, subjects with COPD reported significantly more moderate and severe episodes of acute respiratory disease compared to control groups (Table 1; P<0.001). Associations between individual biomarkers and exacerbations in the 12 months prior to enrollment in COPDGene were performed with adjustments for covariates (SGRQ score, FEV$_1$%, gender, gastroesophageal disease). 20 biomarkers were associated with acute episodes of airways disease requiring prednisone and antibiotics (moderate and severe) and 30 biomarkers were associated with hospitalizations for acute episodes of airway disease (Table 3 and 4).

TABLE 3

Biomarkers associated with moderate or severe episodes of acute airway disease in 12 months prior to enrollment in COPDGene (adjusted for FEV1 %, SGRQ, gender and GERD)

| Biomarker | NB B | NB SE | NB P | Gamma B | Gamma SE | Gamma P |
|---|---|---|---|---|---|---|
| A2M | 0.064528 | 0.098235 | 0.5113 | −1.367921 | 3.166092 | 0.6657 |
| ADIPOQ | 0.081518 | 0.082532 | 0.3233 | 0.258507 | . | . |
| APCS | −0.136676 | 0.085045 | 0.1080 | −0.872489 | 1.042188 | 0.4025 |
| APOA4 | −0.047556 | 0.075820 | 0.5305 | −12.158565 | 14.907162 | 0.4147 |
| AXL | 0.078339 | 0.070078 | 0.2636 | 0.229506 | . | . |
| B2M | 0.140425 | 0.081521 | 0.0850 | −317.357045 | 78.400146 | <.0001 |
| C3 | −0.015357 | 0.091325 | 0.8665 | −1.653495 | 1.932202 | 0.3921 |

TABLE 3-continued

Biomarkers associated with moderate or severe episodes of acute airway disease in 12 months prior to enrollment in COPDGene (adjusted for FEV1 %, SGRQ, gender and GERD)

| Biomarker | NB B | NB SE | NB P | Gamma B | Gamma SE | Gamma P |
|---|---|---|---|---|---|---|
| CCL16 | 0.110559 | 0.075178 | 0.1414 | 0.119469 | . | . |
| CCL18 | 0.123602 | 0.076055 | 0.1041 | 0.487202 | . | . |
| CCL22 | 0.096820 | 0.084338 | 0.2510 | 1.251043 | 0.963607 | 0.1942 |
| CCL23 | 0.048617 | 0.085078 | 0.5677 | −0.956831 | 6.398560 | 0.8811 |
| CCL24 | −0.080904 | 0.078156 | 0.3006 | 179.960441 | 115.713919 | 0.1199 |
| CCL4 | 0.159465 | 0.074961 | 0.0334 | −0.024912 | . | . |
| CCL5 | −0.089408 | 0.090829 | 0.3249 | −0.923787 | 0.811547 | 0.2550 |
| CDH1 | 0.073533 | 0.080325 | 0.3600 | 1.528872 | 1.782482 | 0.3910 |
| CDH13 | −0.000809 | 0.087536 | 0.9926 | −2.870344 | 7.649553 | 0.7075 |
| CEACAM1 | −0.015980 | 0.092957 | 0.8635 | −2.000365 | 1.327408 | 0.1318 |
| CHGA | 0.041851 | 0.084605 | 0.6208 | −0.604732 | 1.007946 | 0.5485 |
| CRP | 0.075465 | 0.078050 | 0.3336 | −0.639013 | . | . |
| CSTB | 0.022802 | 0.086065 | 0.7911 | −5.341694 | 5.546891 | 0.3355 |
| CXCL10 | 0.028490 | 0.074027 | 0.7003 | −0.028153 | . | . |
| CXCL9 | 0.033267 | 0.078109 | 0.6702 | 0.693491 | . | . |
| DCN | 0.167600 | 0.085273 | 0.0494 | 0.884249 | 4.112891 | 0.8298 |
| F7 | −0.132585 | 0.075358 | 0.0785 | −0.431055 | . | . |
| FTL_FTH1 | 0.029829 | 0.078735 | 0.7048 | 0.228806 | . | . |
| GC | −0.016202 | 0.091258 | 0.8591 | −2.737896 | 1.056345 | 0.0095 |
| ICAM1 | 0.104928 | 0.074717 | 0.1602 | 1.081952 | . | . |
| IgM | 0.147241 | 0.074940 | 0.0494 | 233.667152 | 107.568781 | 0.0298 |
| IL16 | 0.162077 | 0.071772 | 0.0239 | −0.080032 | . | . |
| IL18BP | 0.159476 | 0.074320 | 0.0319 | 230.283009 | 107.991830 | 0.0330 |
| IL2RA | 0.152237 | 0.074970 | 0.0423 | 0.552444 | . | . |
| IL6R | −0.079244 | 0.083822 | 0.3445 | −1.440029 | 0.948270 | 0.1289 |
| KIT | 0.071812 | 0.083022 | 0.3871 | 1.633732 | 2.562384 | 0.5237 |
| MB | 0.075521 | 0.090779 | 0.4055 | −1.366233 | 2.172431 | 0.5294 |
| MMP3 | 0.114981 | 0.091205 | 0.2074 | −7.896536 | 7.466145 | 0.2902 |
| PECAM1 | 0.023103 | 0.072410 | 0.7497 | −0.174684 | . | . |
| SELE | −0.004063 | 0.076526 | 0.9577 | −287.191583 | 92.080067 | 0.0018 |
| SERPINA1 | 0.268103 | 0.075081 | 0.0004 | −0.735641 | . | . |
| SERPINA7 | −0.039104 | 0.077345 | 0.6132 | 0.575974 | . | . |
| SFTPD | 0.113685 | 0.083994 | 0.1759 | −1.370209 | 1.312599 | 0.2965 |
| SHBG | 0.079159 | 0.081922 | 0.3339 | 1.747962 | 1.453889 | 0.2293 |
| SLPI | 0.115082 | 0.076856 | 0.1343 | 106.617549 | 0.657874 | <.0001 |
| SOD1 | 0.070077 | 0.072666 | 0.3349 | −0.377605 | . | . |
| SORT1 | −0.020639 | 0.090144 | 0.8189 | −0.613395 | 1.099175 | 0.5768 |
| SPINK1 | 0.082417 | 0.071171 | 0.2469 | 0.175929 | . | . |
| TGFB1_LAP | −0.039542 | 0.077664 | 0.6107 | −315.037678 | 76.840024 | <.0001 |
| THBD | 0.063553 | 0.073395 | 0.3865 | −2.911819 | 2.753673 | 0.2903 |
| TIMP1 | 0.100034 | 0.091043 | 0.2719 | 0.981577 | 1.188477 | 0.4089 |
| TIMP2 | 0.109982 | 0.067601 | 0.1038 | 0.179489 | . | . |
| TNFRSF10C | 0.128177 | 0.079655 | 0.1076 | −8.658054 | 5.687262 | 0.1279 |
| TNFRSF11B | 0.067936 | 0.077028 | 0.3778 | 0.162384 | . | . |
| TNFRSF1A | −0.022268 | 0.092199 | 0.8092 | −1.374140 | 0.616627 | 0.0258 |
| TNFRSF1B | 0.137617 | 0.074243 | 0.0638 | 147.690839 | 135.828613 | 0.2769 |
| VCAM1 | 0.138108 | 0.073046 | 0.0587 | 0.284916 | . | . |
| FGA_FGB_FGG | 0.137680 | 0.079976 | 0.0852 | 1.562703 | 1.343998 | 0.2449 |
| IL18 | 0.019625 | 0.080287 | 0.8069 | −439.669393 | 79.025678 | <.0001 |
| LPA | −0.027305 | 0.085523 | 0.7495 | −0.857016 | 0.598677 | 0.1523 |
| MMP9 | 0.049616 | . | . | −0.612151 | 868.145810 | 0.9994 |
| NPPB_PH | 0.133472 | 0.075147 | 0.0757 | −0.416595 | . | . |
| NRCAM | 0.165310 | 0.094533 | 0.0803 | 0.951112 | 3.303613 | 0.7734 |
| SERPINA3 | −0.074096 | 0.082669 | 0.3701 | −0.660587 | 0.539708 | 0.2210 |
| CCL2 | 0.042438 | 0.082963 | 0.6090 | −2.716479 | 2.782283 | 0.3289 |
| CCL8 | 0.006292 | 0.101283 | 0.9505 | −1.422363 | 1.404356 | 0.3111 |
| IgA | 0.040483 | 0.075711 | 0.5929 | 0.396179 | . | . |
| ANGPT1 | −0.089356 | 0.082159 | 0.2768 | −1.264333 | 1.413424 | 0.3710 |
| BDNF | −0.086599 | 0.092438 | 0.3488 | −1.061689 | 1.046728 | 0.3104 |
| CKM_CKB | 0.032064 | 0.087839 | 0.7151 | −2.906581 | 2.686477 | 0.2793 |
| MDK | 0.047009 | 0.075053 | 0.5311 | 0.071073 | . | . |
| KITLG | 0.075651 | 0.083915 | 0.3673 | −1.393916 | 1.403172 | 0.3205 |
| SERPINE1 | −0.059182 | 0.077999 | 0.4480 | −6.710905 | 4.952651 | 0.1754 |
| CXCL5 | −0.016295 | 0.097975 | 0.8679 | −0.978378 | 0.850357 | 0.2499 |
| VWF | 0.076995 | 0.084810 | 0.3640 | 0.682085 | 1.751311 | 0.6969 |
| AGER | 0.097353 | 0.078061 | 0.2123 | −0.197301 | . | . |
| HGF | 0.129806 | 0.083636 | 0.1207 | −1.765623 | 4.131078 | 0.6691 |
| IL8 | 0.087671 | 0.076985 | 0.2548 | 0.341952 | . | . |
| VEGFA | −0.022738 | 0.090616 | 0.8019 | −1.019436 | 0.741838 | 0.1694 |
| HP | −0.054074 | 0.085563 | 0.5274 | 1.511215 | 2.407880 | 0.5303 |
| CCL13 | 0.105808 | 0.097981 | 0.2802 | −0.835362 | 1.181513 | 0.4795 |
| FAS | 0.122278 | 0.076374 | 0.1094 | −37.570923 | 0.430153 | <.0001 |
| LTF | 0.054899 | 0.079116 | 0.4877 | −3.934146 | 7.554494 | 0.6025 |
| IFNG | 0.035355 | 0.072507 | 0.6258 | 0.238822 | . | . |
| CA9 0 | 0.054074 | 0.176178 | 0.7589 | −17.677049 | . | . |

TABLE 3-continued

Biomarkers associated with moderate or severe episodes of acute airway disease in 12 months prior to enrollment in COPDGene (adjusted for FEV1 %, SGRQ, gender and GERD)

| Biomarker | NB B | NB SE | NB P | Gamma B | Gamma SE | Gamma P |
|---|---|---|---|---|---|---|
| CCL11 0 | −0.064180 | 0.149196 | 0.6671 | −0.448241 | . | . |
| CCL20 0 | −0.275415 | 0.157777 | 0.0809 | −0.423328 | . | . |
| CCL3 0 | −0.301094 | 0.191033 | 0.1150 | −2.496925 | . | . |
| IgE 0 | −0.194264 | 0.151799 | 0.2006 | −3.353686 | . | . |
| IL10 0 | 0.146005 | 0.245385 | 0.5518 | 19.235715 | 0.527476 | <.0001 |
| IL12B 0 | −0.184935 | 0.174487 | 0.2892 | −18.337859 | . | . |
| IL15 0 | −0.132093 | 0.182757 | 0.4698 | −17.049353 | . | . |
| IL17A 0 | −0.525894 | 0.334025 | 0.1154 | −19.671730 | . | . |
| IL1RN 0 | 0.177593 | 0.194112 | 0.3602 | 18.144964 | 0.694093 | <.0001 |
| IL23A 0 | −0.066965 | 0.213279 | 0.7535 | 18.806752 | 0.798742 | <.0001 |
| INS_intact 0 | −0.013736 | 0.299864 | 0.9635 | −18.694674 | . | . |
| INS_total 0 | −0.104754 | 0.275286 | 0.7036 | −17.941589 | . | . |
| KLK3_F 0 | 0.253262 | 0.507067 | 0.6175 | 17.183559 | 1.421171 | <.0001 |
| MDA_LDL 0 | −0.245806 | 0.179309 | 0.1704 | −3.564266 | . | . |
| MICA 0 | 0.143992 | 0.181545 | 0.4277 | 18.211769 | 0.692406 | <.0001 |
| OLR1 0 | −0.200556 | 0.281777 | 0.4766 | −0.140208 | . | . |

NB B = negative binomial coefficient;
NB SE = negative binomial coefficient standard error;
NB P = probability that NB B is zero;
Gamma is from zero inflation model; (a negative binomial model with zero inflation)

TABLE 4

Biomarkers associated with hospitalizations for acute airway disease in 12 months prior to enrollment in COPDGene (adjusted for FEV1 %, SGRQ, gender and GERD)

| Biomarker | NB B | NB SE | NB P | Gamma B | Gamma SE | Gamma P |
|---|---|---|---|---|---|---|
| A2M | −0.241809 | 0.212894 | 0.2560 | −1.044216 | 1.122284 | 0.3521 |
| ADIPOQ | −0.089329 | 0.199417 | 0.6542 | −0.466993 | 0.916319 | 0.6103 |
| APCS | −0.299773 | 0.166051 | 0.0710 | −1.345774 | 4.923690 | 0.7846 |
| APOA4 | −0.446526 | 0.204130 | 0.0287 | −1.782041 | 0.813814 | 0.0285 |
| AXL | 0.073085 | 0.159323 | 0.6464 | −0.904254 | 0.501889 | 0.0716 |
| B2M | 0.417983 | 0.248387 | 0.0924 | 0.591672 | 0.939841 | 0.5290 |
| C3 | −0.000529 | 0.198880 | 0.9979 | 1.001656 | 1.015508 | 0.3240 |
| CCL16 | −0.173945 | 0.143174 | 0.2244 | −168.719201 | 141.375012 | 0.2327 |
| CCL18 | −0.008260 | 0.190600 | 0.9654 | −0.261351 | 0.497118 | 0.5991 |
| CCL22 | 0.080036 | 0.167006 | 0.6318 | 0.405946 | 0.336934 | 0.2283 |
| CCL23 | 0.261274 | 0.188093 | 0.1648 | 0.635430 | 1.075216 | 0.5545 |
| CCL24 | −0.046743 | 0.185696 | 0.8013 | −0.362568 | 0.418178 | 0.3859 |
| CCL4 | −0.042380 | 0.154651 | 0.7841 | −688.803966 | 92.255257 | <.0001 |
| CCL5 | −0.441052 | 0.166113 | 0.0079 | −0.150705 | 0.506231 | 0.7659 |
| CDH1 | 0.102698 | 0.201539 | 0.6104 | 0.318758 | 1.404673 | 0.8205 |
| CDH13 | −0.269965 | 0.169126 | 0.1104 | −5.800987 | 3.859801 | 0.1329 |
| CEACAM1 | 0.119335 | 0.226160 | 0.5977 | 0.451568 | 1.687940 | 0.7891 |
| CHGA | 0.060578 | 0.178193 | 0.7339 | 0.246290 | 0.606286 | 0.6846 |
| CRP | 0.230848 | 0.138241 | 0.0949 | 316.892315 | 65.676690 | <.0001 |
| CSTB | −0.189351 | 0.201562 | 0.3475 | −2.066258 | 1.100505 | 0.0604 |
| CXCL10 | 0.039258 | 0.190277 | 0.8365 | −0.282832 | 0.401212 | 0.4808 |
| CXCL9 | 0.125957 | 0.139340 | 0.3660 | −0.129611 | 998.842832 | 0.9999 |
| DCN | 0.018076 | 0.154764 | 0.9070 | −0.185208 | 0.616577 | 0.7639 |
| F7 | −0.192945 | 0.168497 | 0.2522 | −0.014814 | 1.175570 | 0.9899 |
| FTL_FTH1 | −0.066095 | 0.141985 | 0.6416 | −603.864369 | 65.123072 | <.0001 |
| GC | −0.315901 | 0.221910 | 0.1546 | −1.566829 | 0.998773 | 0.1167 |
| ICAM1 | 0.515710 | 0.186449 | 0.0057 | 0.449753 | 0.607085 | 0.4588 |
| IgM | −0.020509 | 0.139324 | 0.8830 | −0.076985 | . | . |
| IL16 | −0.046901 | 0.157005 | 0.7652 | −0.677165 | 0.408599 | 0.0975 |
| IL18BP | 0.357923 | 0.158507 | 0.0239 | −0.092246 | 0.654107 | 0.8878 |
| IL2RA | 0.267025 | 0.194038 | 0.1688 | −0.284972 | 0.694945 | 0.6818 |
| IL6R | 0.222878 | 0.226026 | 0.3241 | 0.846488 | 2.009774 | 0.6736 |
| KIT | −0.009806 | 0.158534 | 0.9507 | 0.292581 | 0.458514 | 0.5234 |
| MB | −0.129749 | 0.152712 | 0.3955 | −130.121701 | 277.853431 | 0.6396 |
| MMP3 | 0.028684 | 0.344497 | 0.9336 | −2.276561 | 9.644191 | 0.8134 |
| PECAM1 | 0.055118 | 0.130939 | 0.6738 | 0.109134 | . | . |
| SELE | 0.208584 | 0.182098 | 0.2520 | 0.247316 | 1.267840 | 0.8453 |
| SERPINA1 | 0.673086 | 0.206252 | 0.0011 | 1.528146 | 0.985311 | 0.1209 |
| SERPINA7 | −0.055159 | 0.215798 | 0.7983 | −0.397180 | 0.971641 | 0.6827 |
| SFTPD | 0.146991 | 0.198532 | 0.4591 | −0.540496 | 0.652574 | 0.4075 |
| SHBG | 0.247936 | 0.165267 | 0.1336 | 3.579999 | 3.070030 | 0.2436 |
| SLPI | 0.228753 | 0.189056 | 0.2263 | 0.575665 | 0.848797 | 0.4976 |
| SOD1 | −0.189236 | 0.135207 | 0.1616 | 0.136348 | . | . |
| SORT1 | −0.041637 | 0.210876 | 0.8435 | −0.565226 | 0.520185 | 0.2772 |

TABLE 4-continued

Biomarkers associated with hospitalizations for acute airway disease in 12 months
prior to enrollment in COPDGene (adjusted for FEV1 %, SGRQ, gender and GERD)

| Biomarker | NB B | NB SE | NB P | Gamma B | Gamma SE | Gamma P |
|---|---|---|---|---|---|---|
| SPINK1 | 0.351665 | 0.132386 | 0.0079 | 0.344807 | 0.279105 | 0.2167 |
| TGFB1_LAP | −0.407230 | 0.170402 | 0.0169 | −0.390683 | 0.539246 | 0.4688 |
| THBD | 0.123378 | 0.129101 | 0.3392 | −238.957237 | 104.994010 | 0.0229 |
| TIMP1 | −0.090598 | 0.137970 | 0.5114 | −210.221550 | 168.912324 | 0.2133 |
| TIMP2 | 0.024506 | 0.182370 | 0.8931 | 0.174175 | 0.468645 | 0.7101 |
| TNFRSF10C | −0.016889 | 0.159730 | 0.9158 | −415.250792 | 215.389404 | 0.0539 |
| TNFRSF11B | −0.150193 | 0.173408 | 0.3864 | −0.222151 | 0.922218 | 0.8096 |
| TNFRSF1A | −0.002748 | 0.237745 | 0.9908 | −1.400497 | 0.848379 | 0.0988 |
| TNFRSF1B | 0.242545 | 0.219363 | 0.2689 | −0.807552 | 1.280250 | 0.5282 |
| VCAM1 | 0.178006 | 0.166605 | 0.2853 | −0.473419 | 0.316744 | 0.1350 |
| FGA_FGB_FGG | −0.005139 | 0.198339 | 0.9793 | −0.379748 | 1.693361 | 0.8226 |
| IL18 | 0.089720 | 0.234913 | 0.7025 | −0.883242 | 0.637312 | 0.1658 |
| LPA | −0.056014 | 0.159414 | 0.7253 | −2.021539 | 6.382970 | 0.7515 |
| MMP9 | −0.013561 | 0.137888 | 0.9217 | −0.348188 | . | . |
| NPPB_PH | 0.203177 | 0.135012 | 0.1324 | 0.109309 | . | . |
| NRCAM | 0.167175 | 0.133134 | 0.2092 | −0.032562 | 294.535122 | 0.9999 |
| SERPINA3 | 0.028402 | 0.141690 | 0.8411 | 167.718441 | 95.026806 | 0.0776 |
| CCL2 | −0.108676 | 0.173457 | 0.5310 | −0.249440 | 0.419765 | 0.5524 |
| CCL8 | −0.283070 | 0.196491 | 0.1497 | −1.092187 | 0.669190 | 0.1027 |
| IgA | −0.033340 | 0.136571 | 0.8071 | 0.175901 | 345.973496 | 0.9996 |
| ANGPT1 | −0.458108 | 0.165232 | 0.0056 | −0.670828 | 0.622692 | 0.2813 |
| BDNF | −0.518180 | 0.174963 | 0.0031 | −0.075255 | 0.432847 | 0.8620 |
| CKM_CKB | −0.336683 | 0.206715 | 0.1034 | −1.151950 | 0.669339 | 0.0852 |
| MDK | 0.097580 | 0.200156 | 0.6259 | −0.271703 | 3.520990 | 0.9385 |
| KITLG | 0.048212 | 0.129824 | 0.7104 | 0.004373 | . | . |
| SERPINE1 | −0.536450 | 0.154229 | 0.0005 | −4.734640 | 6.253283 | 0.4490 |
| CXCL5 | −0.624196 | 0.200746 | 0.0019 | −0.842371 | 0.667638 | 0.2070 |
| VWF | 0.028570 | 0.132590 | 0.8294 | −0.048378 | . | . |
| AGER | 0.698411 | 0.168658 | <.0001 | 1.023391 | 0.439645 | 0.0199 |
| HGF | −0.030798 | 0.182530 | 0.8660 | −0.509803 | 1.725076 | 0.7676 |
| IL8 | 0.021335 | 0.134992 | 0.8744 | −0.005056 | . | . |
| VEGFA | −0.187405 | 0.165596 | 0.2578 | −0.419354 | 0.348614 | 0.2290 |
| HP | −0.057698 | 0.189324 | 0.7606 | 0.620277 | 1.060428 | 0.5586 |
| CCL13 | −0.121122 | 0.149563 | 0.4180 | −656.938342 | 59.316461 | <.0001 |
| FAS | −0.000739 | 0.138960 | 0.9958 | −233.469986 | 8.306099 | <.0001 |
| LTF | −0.021575 | 0.136091 | 0.8740 | 0.257628 | 743.047342 | 0.9997 |
| IFNG | 0.014045 | 0.133301 | 0.9161 | −0.214921 | 721.926456 | 0.9998 |
| CA9 0 | 0.098290 | 0.450892 | 0.8274 | −14.871186 | . | . |
| CCL11 0 | −0.009931 | 0.454508 | 0.9826 | 15.236634 | 3.418052 | <.0001 |
| CCL20 0 | −0.418010 | 0.494842 | 0.3983 | 17.443009 | 0.904449 | <.0001 |
| CCL3 0 | 0.282492 | 0.429761 | 0.5110 | 18.689217 | 0.529444 | <.0001 |
| IgE 0 | −0.026653 | 0.451606 | 0.9529 | 17.368899 | 0.764092 | <.0001 |
| IL10 0 | 0.155459 | 0.514562 | 0.7626 | 18.092972 | 0.681601 | <.0001 |
| IL12B 0 | −0.604121 | 0.422629 | 0.1529 | −18.278624 | . | . |
| IL15 0 | −0.220127 | 0.455995 | 0.6293 | −15.250660 | . | . |
| IL17A 0 | 0.357547 | 0.773156 | 0.6438 | 15.088348 | 5.770551 | 0.0089 |
| IL1RN 0 | 0.528039 | 0.512668 | 0.3030 | 14.719064 | 1.806566 | <.0001 |
| IL23A 0 | 0.672307 | 0.465195 | 0.1484 | 17.606857 | 0.532548 | <.0001 |
| INS_intact 0 | −0.105176 | 0.619856 | 0.8653 | −16.879610 | . | . |
| INS_total 0 | −0.076414 | 0.580083 | 0.8952 | −14.991322 | . | . |
| KLK3_F 0 | 0.860823 | 0.816469 | 0.2917 | 17.416145 | 0.720743 | <.0001 |
| MDA_LDL 0 | −0.352323 | 0.448761 | 0.4324 | 17.591840 | 0.640241 | <.0001 |
| MICA 0 | 0.925802 | 0.402440 | 0.0214 | 18.243832 | 0.390632 | <.0001 |
| OLR1 0 | −0.025457 | 0.542261 | 0.9626 | 18.652550 | 0.584472 | <.0001 |

NB B = negative binomial coefficient;
NB SE = negative binomial coefficient standard error;
NB P = probability that NB B is zero;
Gamma is from zero inflation model; (a negative binomial model with zero inflation)

Plasma Biomarkers Predictive of Exacerbations after Enrollment

Figure 2:
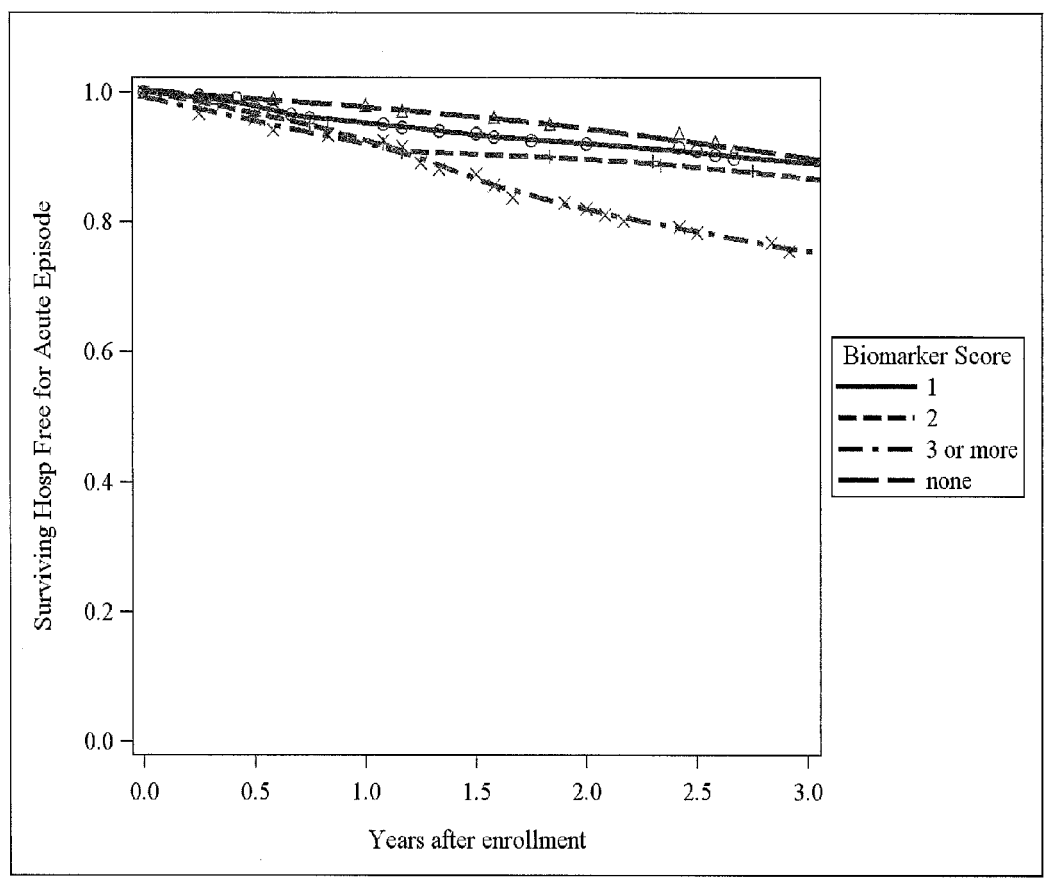
FIG. 2 shows risk of hospitalization for exacerbation of COPD based on number of abnormal biomarkers.

Subjects were followed for 3.1±0.8 years after enrollment and assessed every six months for new exacerbations. 20% of subjects without COPD and 56% of subjects with COPD reported at least one episode of acute airway disease requiring antibiotics or prednisone during the follow up period; 2% of control and 25% of COPD subjects reported at least one hospitalization for an acute episode airways disease during follow up. Cox proportional hazards multiple biomarker modeling with adjustment for clinical covariates revealed 7 biomarkers independently associated with time to first episode of acute airway disease (Table 5) and 7 biomarkers independently associated with time to first hospitalization for acute airway disease (Table 6). Both chemokine (C-C motif) ligand 24 (CCL24) and interleukin 2 receptor-α (IL2RA) were independently associated with antibiotic/corticosteroid treatment and hospitalization for acute episodes of airway disease (FIGS. 1 and 2). Apolipoprotein A-IV (APOA4), Group-specific component (vitamin D binding protein) (GC), Immunoglobulin A (IgA), Lipoprotein A (LPA), and Kallikrein-related peptidase 3 (KLK3) were associated with antibiotic/corticosteroid treatment but not hospitalization. Fas cell surface death receptor (FAS), Neuronal cell adhesion molecule (NRCAM), Tumor necrosis factor receptor superfamily, member 10c, decoy without an intracellular domain (TNFRSF10C), Interleukin 12 subunit p40 (IL12B), and Interleukin 23, α-subunit p19 (IL23A) were associated only with hospitalization.

TABLE 5

Factors independently associated with acute episodes of respiratory disease treated with antibiotics or corticosteroids on longitudinal follow-up

| Risk Factor | HR (95% CI) | Pr > ChiSq |
|---|---|---|
| SGRQ score (per 4 units) | 1.10 (1.06-1.13) | <.0001 |
| Exacerbation Frequency in prior 12 months (per event) | 1.23 (1.13-1.34) | <.0001 |
| $FEV_1$ % post bronchodilator (per 10%) | 0.92 (0.86-0.98) | 0.0090 |
| CCL24 (per SD) | 0.83 (0.72-0.95) | 0.0067 |
| IL2RA (per SD) | 1.28 (1.11-1.47) | 0.0006 |
| APOA4 (per SD) | 0.87 (0.77-0.99) | 0.0417 |
| GC (per SD) | 1.15 (1.00-1.31) | 0.0471 |
| IgA (per SD) | 0.80 (0.69-0.91) | 0.0011 |
| LPA (per SD) | 1.29 (1.13-1.46) | 0.0001 |
| KLK3_F (above LLOQ) | 0.66 (0.51-0.86) | 0.0019 |

HR = hazard ratio (adjusted odds ratio)

TABLE 6

Factors independently associated with hospitalizations from acute episodes of respiratory disease on longitudinal follow-up

| Risk Factor | HR (95% CI) | Pr > ChiSq |
|---|---|---|
| SGRQ score (per 4 units) | 1.14 (1.08-1.20) | <.0001 |
| Exacerbation Frequency in prior 12 months (per event) | 1.33 (1.17-1.53) | <.0001 |
| $FEV_1$ % post bronchodilator (per 10%) | 0.84 (0.75-0.93) | 0.0013 |
| CCL24 (per SD) | 0.72 (0.57-0.91) | 0.0064 |
| IL2RA (per SD) | 1.49 (1.17-1.90) | 0.0012 |
| FAS (per SD) | 0.77 (0.62-0.96) | 0.0190 |
| NRCAM (per SD) | 1.33 (1.06-1.69) | 0.0154 |
| TNFRSF10C (per SD) | 0.73 (0.58-0.91) | 0.0060 |
| IL12B (above LLOQ) | 1.83 (1.12-3.00) | 0.0165 |
| IL23A (above LLOQ) | 1.66 (1.02-2.70) | 0.0402 |

HR = hazard ratio (adjusted odds ratio)

Example 2

This example shows that there is a biomarker signature of emphysema in peripheral blood that can provide information about the presence and distribution of emphysema in chronic obstructive pulmonary disease (COPD).

COPD is a phenotypically heterogeneous disease. In COPD, the presence of emphysema phenotype is associated with increased mortality and increased risk of lung cancer and its distribution has implications for treatments. High resolution computed tomography (HRCT) chest scans are useful in characterizing the extent and distribution of emphysema but increase cost and raise concerns about radiation exposure. Systemic biomarkers may provide additional information in differentiating COPD phenotypes. Methods: 114 plasma biomarkers were measured using a custom assay in 588 individuals enrolled in the COPDGene study. Quantitative emphysema measurements included percent low lung attenuation (% LAA)≤-950 HU, ≤-910 HU and mean lung attenuation at the $15^{th}$ percentile on lung attenuation curve (LP15A). Multiple regression analysis was performed to determine plasma biomarkers associated with emphysema independent of covariates age, gender, smoking status, body mass index and $FEV_1$. The findings were subsequently validated using baseline blood samples from a separate cohort of 388 subjects enrolled in the Treatment of Emphysema with a Selective Retinoid Agonist (TESRA) study.

Results: Regression analysis identified multiple biomarkers associated with CT-assessed emphysema in COPDGene, including advanced glycosylation end-products receptor (AGER or RAGE, p<0.001), intercellular adhesion molecule 1 (ICAM, p<0.001), and chemokine ligand 20 (CCL20, p<0.001). Validation in the TESRA cohort revealed significant associations with RAGE, ICAM1, and CCL20 with radiologic emphysema (p<0.001 after meta-analysis). Other biomarkers that were associated with emphysema include CDH1, CDH 13 and SERPINA7, but were not available for validation in the TESRA study.

Conclusions: Peripheral blood biomarkers including sRAGE, ICAM1 and CCL20 can be useful in evaluating the presence and distribution of emphysema in COPD, and can have a role to play in understanding the pathogenesis and phenotypic heterogeneity of emphysema.

Study Population

COPDGene is a multi-centered study of the genetic epidemiology of COPD that enrolled 10,192 non-Hispanic White and African-American individuals, aged 45-80 years old with at least a 10 pack-year history of smoking, who had not had an exacerbation of COPD for at least the previous 30 days. Additional information on the COPDGene study and the collection of clinical data has been described previously (Regan E A., et al. Genetic epidemiology of copd (copedgene) study design. *Copd*. 2010;7:32-43). 1839 COPDGene subjects (1599 non-Hispanic White (NHW) and 240 non-Hispanic Black) had fresh frozen plasma collected using a p100 tube (BD) at five COPDGene sites. From this cohort a subset of 602 NHW subjects (no non-Hispanic Black subjects included due to limited numbers) were selected for a comprehensive biomarker study with an attempt to obtain a range of GOLD stages and match groups as closely as possible based on age, gender and smoking history. Of the 602 subjects, 588 subjects had quantitative HRCT measurements available.

A separate validation cohort of 388 individuals (all former smokers with COPD) was obtained from the Treatment of Emphysema with a Selective Retinoid Agonist (TESRA) study. TESRA was a multi-centered randomized controlled trial assessing the safety and efficacy of palovarotene in ex-smokers with COPD. Only baseline samples before treatment were used for biomarker determination. Emphysema was quantitatively assessed by low dose spiral CT in the TESRA cohort. Additional information on the TESRA study has been described previously (Jones P W., Tesra (treatment of emphysema with selective retinoid agonist) study results. *American journal of respiratory and critical care medicine* 2011;183:A6418).

Clinical Data and Definitions

COPD was defined as post bronchodilator ratio of forced expiratory volume in the first second ($FEV_1$) to forced vital capacity (FVC)<0.70. Current or ex-smokers without spirometric evidence of airflow obstruction ($FEV_1$/FVC>0.70) were classified as controls (Vestbo J., et al. Global strategy for the diagnosis, management, and prevention of chronic obstructive pulmonary disease: GOLD executive summary. *Am J Respir Crit Care Med.* Feb. 15, 2013;187(4):347-365).

COPDGene study patients underwent whole lung volumetric multi-detector computed tomography (CT) as previously described (Regan E A., et al. Genetic epidemiology of copd (copedgene) study design. *Copd*. 2010;7:32-43; Han M K., et al. Chronic obstructive pulmonary disease exacerbations in the COPDGene study: associated radiologic phenotypes. *Radiology*. October 2011;261(1):274-282). Quantitative analysis of lung density was performed using the Slicer software package (www.slicer.org).

Emphysema was primarily quantified by the percent of lung voxels (% LAA)≤-950 HU on the inspiratory images of CT scans for the whole lung. Emphysema was additionally quantified by percent of lung voxels (% LAA)≤-910 HU on inspiratory CT scans and as mean lung attenuation at the 15$^{th}$ percentile on lung volume-adjusted attenuation curve (LP15A). In the TESRA cohort emphysema was quantified as % LAA≤-910 HU and LP15A on HRCT scans (Jones P W., Tesra (treatment of emphysema with selective retinoid agonist) study results. *American journal of respiratory and critical care medicine* 2011;183:A6418). Densiometric analyses of the HRCTs were completed in a central lab (BioClinica, Leiden, The Netherlands) using PulmoCMS software (Medis specials, Leiden, The Netherlands). The study design and clinical outcomes have been previously reported (Cheng D T., et al. Systemic soluble receptor for advanced glycation endproducts is a biomarker of emphysema and associated with AGER genetic variants in patients with chronic obstructive pulmonary disease. *Am J Respir Crit Care Med*. Oct. 15, 2013;188(8):948-957; Jones P W., Tesra (treatment of emphysema with selective retinoid agonist) study results. *American journal of respiratory and critical care medicine* 2011;183:A6418).

Biomarker Selection and Measurement

For the COPDGene cohort, 114 candidate biomarkers were selected based on a review of the literature and previously reported pilot work from the BIOSPIR group (O'Neal W K., et al. Comparison of serum, EDTA plasma and P100 plasma for luminex-based biomarker multiplex assays in patients with chronic obstructive pulmonary disease in the SPIROMICS study. *J Transl Med*. 2014;12:9). Biomarker levels were determined using a custom 15-panel assay created by Myriad-RBM (Austin, Tex.) multiplex technology. Blood samples were drawn from non-fasting individuals. Approximately 8.5 mL of blood was withdrawn from the ante-cubital vein into a sterile 13×1000 mm P100 Blood Collection Tube (BD, New Jersey, USA). The sample was immediately centrifuged at 2500×g, 20 minutes at room temperature. Aliquots in 500 μL tubes were stored at −80° C. until analyzed. In the TESRA cohort, 111 similarly chosen protein biomarkers were measured in ethylenediamine-tetraacetic acid (EDTA) plasma in duplicate at Rules Based Medicine (Austin, Tex.) and Quest Diagnostics (Valencia, Calif.). A full list of biomarkers analyzed in the TESRA study has been published (Cheng D T., et al. Systemic soluble receptor for advanced glycation endproducts is a biomarker of emphysema and associated with AGER genetic variants in patients with chronic obstructive pulmonary disease. *Am J Respir Crit Care Med*. Oct. 15, 2013;188(8): 948-957)

Statistical Analysis

Differences in demographic characteristics of study subjects were analyzed using a t-test for continuous variables and a Chi-squared test for categorical variables. Emphysema severity was classified as none, mild, moderate and severe. For % LAA≤-950 HU the cutoffs were <5%, 5-<10%, 10-<20% and ≥20%, respectively, while for % LAA ≤-910 HU the cutoffs were <35%, 35-<45%, 45-<55% and ≥55%, respectively. Cutoffs were based on mean values from COPDGene studies and balancing the sample size in each group (Schroeder J D., et al. Relationships between airflow obstruction and quantitative CT measurements of emphysema, air trapping, and airways in subjects with and without chronic obstructive pulmonary disease. *AJR Am J Roentgenol*. September 2013;201 (3):W460-470).

Biomarkers (n=17) with >10% and <95% of values below the lower limit of quantitation (LLOQ) for that particular biomarker were transformed into binary variables (present or absent). Biomarkers (n=16) with >95% values below LLOQ were excluded from the analysis. For regression analysis, the remaining biomarker levels (n=81) underwent an empirical normal quantile transformation projecting the ranks onto an inverse normal distribution so that they resemble a normal distribution and allow comparison of biomarkers at different concentrations. Non-transformed biomarker levels are also presented (Table 7). Collinearity among biomarkers and covariates was assessed using Pearson correlation. Collinearity (R>0.6) was observed between proinsulin intact (INS intact) and proinsulin total (INS total) so INS intact was removed from the analysis. Also, brain derived neurotropic factor (BDNF) was removed, as it was collinear with angiopoietin 1, CCL5 (T cell specific protein RANTES), epithelial-derived neutrophil-activating protein 78, alpha-1 antitrypsin and latency associated peptide of transforming growth factor beta 1. For modeling of multiple biomarkers, stepwise regression, with a combination of backwards and forwards selection and a p-value threshold <0.15 for entry and exit from the model, was used to arrive at the final model. A p-value of <0.05 was taken as statistically significant for association with the outcome emphysema variables.

TABLE 7

Biomarkers in COPDGene biomarker study*

| Biomarker Abv. | Biomarker name | Units | Variable type | 25th Percentile | Median | 75$^{th}$ Percentile | LLOQ | % below LLOQ |
|---|---|---|---|---|---|---|---|---|
| A2M | Alpha-2-Macroglobulin (A2Macro) | mg/mL | Continuous | 0.94 | 1 | 1.2 | 0.023 | 0% |
| ADIPO | Adiponectin | ug/mL | Continuous | 3.5 | 5.3 | 8.05 | 0.051 | 0% |
| APCS | Serum Amyloid P-Component (SAP) | ug/mL | Continuous | 14 | 17 | 21 | 0.093 | 0% |
| APOA4 | Apolipoprotein A-IV (Apo A-IV) | ug/mL | Continuous | 66 | 167 | 459.5 | 0.96 | 0% |

TABLE 7-continued

Biomarkers in COPDGene biomarker study*

| Biomarker Abv. | Biomarker name | Units | Variable type | 25th Percentile | Median | 75th Percentile | LLOQ | % below LLOQ |
|---|---|---|---|---|---|---|---|---|
| AXL | AXL Receptor Tyrosine Kinase (AXL) | ng/mL | Continuous | 9.7 | 12 | 15 | 0.050 | 0% |
| B2M | Beta-2-Microglobulin (B2M) | ug/mL | Continuous | 1.4 | 1.8 | 2.3 | 0.0069 | 0% |
| C3 | Complement C3 (C3) | mg/mL | Continuous | 1.1 | 1.2 | 1.4 | 0.020 | 0% |
| CCL16 | Chemokine CC-4 (HCC-4) | ng/mL | Continuous | 4 | 5.3 | 7 | 0.047 | 0% |
| CCL18 | Pulmonary and Activation-Regulated Chemokine (PARC) | ng/mL | Continuous | 63 | 89 | 119.5 | 6.2 | 0% |
| CCL22 | Macrophage-Derived Chemokine (MDC) | pg/mL | Continuous | 308.5 | 400 | 487.75 | 19 | 0% |
| CCL23 | Myeloid Progenitor Inhibitory Factor 1 (MPIF-1) | ng/mL | Continuous | 1.1 | 1.4 | 1.7 | 0.18 | 0% |
| CCL24 | Eotaxin-2 | pg/mL | Continuous | 359 | 553 | 844 | 50 | 0% |
| CCL4 | Macrophage Inflammatory Protein-1 beta (MIP-1 beta) | pg/mL | Continuous | 152.25 | 197 | 255 | 31 | 0% |
| CCL5 | T-Cell-Specific Protein RANTES (RANTES) | ng/mL | Continuous | 5.25 | 9.8 | 17 | 0.024 | 0% |
| CDH1 | Cadherin-1 (E-Cad) | ng/mL | Continuous | 2570 | 3110 | 4000 | 6.0 | 0% |
| CDH13 | Cadherin-13 (T-cad) | ng/mL | Continuous | 15 | 18 | 22 | 2.2 | 0% |
| CEACAM1 | Carcinoembryonic antigen-related cell adhesion molecule 1 (CEACAM1) | ng/mL | Continuous | 12 | 14 | 16 | 3.1 | 0% |
| CHGA | Chromogranin-A (CgA) | ng/mL | Continuous | 334.25 | 485.5 | 774.75 | 13 | 0% |
| CRP | C-Reactive Protein (CRP) | ug/mL | Continuous | 1.3 | 2.7 | 6 | 0.048 | 0% |
| CSTB | Cystatin-B | ng/mL | Continuous | 7.3 | 9.4 | 12 | 0.34 | 0% |
| CXCL10 | Interferon gamma Induced Protein 10 (IP-10) | pg/mL | Continuous | 206 | 262 | 354 | 100 | 0% |
| CXCL9 | Monokine Induced by Gamma Interferon (MIG) | pg/mL | Continuous | 697.5 | 1020 | 1550 | 143 | 0% |
| DCN | Decorin | ng/mL | Continuous | 1.7 | 1.9 | 2.2 | 0.13 | 0% |
| F7 | Factor VII | ng/mL | Continuous | 456 | 563 | 688 | 1.8 | 0% |
| FTL_FTH1 | Ferritin (FRTN) | ng/mL | Continuous | 66 | 120 | 217.5 | 4.3 | 0% |
| GC | Vitamin D-Binding Protein (VDBP) | ug/mL | Continuous | 219.5 | 278 | 348.5 | 5.6 | 0% |
| ICAM1 | Intercellular Adhesion Molecule 1 (ICAM-1) | ng/mL | Continuous | 102 | 125 | 151 | 1.5 | 0% |
| IgM | Immunoglobulin M (IgM) | mg/mL | Continuous | 1.05 | 1.6 | 2.3 | 0.094 | 0% |

TABLE 7-continued

Biomarkers in COPDGene biomarker study*

| Biomarker Abv. | Biomarker name | Units | Variable type | 25th Percentile | Median | 75th Percentile | LLOQ | % below LLOQ |
|---|---|---|---|---|---|---|---|---|
| IL16 | Interleukin-16 (IL-16) | pg/mL | Continuous | 330.25 | 393 | 464.75 | 87 | 0% |
| IL18BP | Interleukin-18-binding protein (IL-18bp) | ng/mL | Continuous | 9.1 | 11 | 14 | 0.096 | 0% |
| IL2RA | Interleukin-2 receptor alpha (IL-2 receptor alpha) | pg/mL | Continuous | 1712.5 | 2100 | 2667.5 | 420 | 0% |
| IL6R | Interleukin-6 receptor (IL-6r) | ng/mL | Continuous | 23 | 28 | 34 | 0.018 | 0% |
| KIT | Mast/stem cell growth factor receptor (SCFR) | ng/mL | Continuous | 6.8 | 8.1 | 9.3 | 0.51 | 0% |
| MB | Myoglobin | ng/mL | Continuous | 24.5 | 34 | 48 | 2.1 | 0% |
| MMP3 | Matrix Metalloproteinase 3 (MMP-3) | ng/mL | Continuous | 5.6 | 8.2 | 12 | 0.049 | 0% |
| PECAM1 | Platelet endothelial cell adhesion molecule (PECAM-1) | ng/mL | Continuous | 37 | 44 | 52 | 11 | 0% |
| SELE | E-Selectin | ng/mL | Continuous | 5.6 | 7.6 | 10 | 0.31 | 0% |
| SERPINA1 | Alpha-1-Antitrypsin (AAT) | mg/mL | Continuous | 1.6 | 1.8 | 2.1 | 0.016 | 0% |
| SERPINA7 | Thyroxine-Binding Globulin (TBG) | ug/mL | Continuous | 32 | 37 | 42 | 0.22 | 0% |
| SFTPD | Pulmonary surfactant-associated protein D (SP-D) | ng/mL | Continuous | 4.7 | 6.6 | 8.8 | 0.19 | 0% |
| SHBG | Sex Hormone-Binding Globulin (SHBG) | nmol/L | Continuous | 39 | 54 | 76.5 | 3.1 | 0% |
| SLPI | Antileukoproteinase (ALP) | ng/mL | Continuous | 33 | 37 | 42 | 0.98 | 0% |
| SOD1 | Superoxide Dismutase 1, soluble (SOD-1) | ng/mL | Continuous | 25 | 32 | 41 | 0.12 | 0% |
| SORT1 | Sortilin | ng/mL | Continuous | 4.9 | 5.8 | 6.9 | 0.22 | 0% |
| SPINK1 | Pancreatic secretory trypsin inhibitor (TATI) | ng/mL | Continuous | 10 | 13 | 18 | 0.16 | 0% |
| TGFB1_LAP | Latency-Associated Peptide of Transforming Growth Factor beta 1 (LAP TGF-b1) | ng/mL | Continuous | 2.5 | 3.8 | 6.2 | 0.13 | 0% |
| THBD | Thrombomodulin (TM) | ng/mL | Continuous | 3.8 | 4.4 | 5.2 | 0.052 | 0% |
| TIMP1 | Tissue Inhibitor of Metalloproteinases 1 (TIMP-1) | ng/mL | Continuous | 63 | 72 | 86.5 | 1.2 | 0% |
| TIMP2 | Tissue Inhibitor of Metalloproteinases 2 (TIMP-2) | ng/mL | Continuous | 59 | 66 | 73 | 1.5 | 0% |

TABLE 7-continued

Biomarkers in COPDGene biomarker study*

| Biomarker Abv. | Biomarker name | Units | Variable type | 25th Percentile | Median | 75th Percentile | LLOQ | % below LLOQ |
|---|---|---|---|---|---|---|---|---|
| TNFRSF10C | TNF-Related Apoptosis-Inducing Ligand Receptor 3 (TRAIL-R3) | ng/mL | Continuous | 9.1 | 13 | 17 | 0.96 | 0% |
| TNFRSF11B | Osteoprotegerin (OPG) | pM | Continuous | 4.5 | 5.5 | 6.6 | 0.45 | 0% |
| TNFRSF1A | Tumor Necrosis Factor Receptor I (TNF RI) | pg/mL | Continuous | 1350 | 1630 | 2017.5 | 36 | 0% |
| TNFRSF1B | Tumor necrosis factor receptor 2 (TNFR2) | ng/mL | Continuous | 4.6 | 5.6 | 7.1 | 0.86 | 0% |
| VCAM1 | Vascular Cell Adhesion Molecule-1 (VCAM-1) | ng/mL | Continuous | 430.5 | 505 | 598 | 2.4 | 0% |
| FGA_FGB_FGG | Fibrinogen | mg/mL | Continuous | 3.6 | 4.2 | 4.8 | 0.049 | 0.17% |
| IL18 | Interleukin-18 (IL-18) | pg/mL | Continuous | 169 | 229 | 301.75 | 41 | 0.17% |
| LPA | Apolipoprotein (a) (Lp(a)) | ug/mL | Continuous | 6.7 | 7.8 | 9.1 | 1.6 | 0.17% |
| MMP9 | Matrix Metalloproteinase-9 (MMP-9) | ng/mL | Continuous | 201 | 299 | 451 | 37 | 0.17% |
| NPPB_PH | N-terminal prohormone of brain natriuretic peptide (NT proBNP) | pg/mL | Continuous | 235 | 460 | 838 | 16 | 0.17% |
| NRCAM | Neuronal Cell Adhesion Molecule (Nr-CAM) | ng/mL | Continuous | 0.695 | 0.9 | 1.2 | 0.20 | 0.17% |
| SERPINA3 | Alpha-1-Antichymotrypsin (AACT) | ug/mL | Continuous | 664.5 | 748 | 861 | 13 | 0.17% |
| CCL2 | Monocyte Chemotactic Protein 1 (MCP-1) | pg/mL | Continuous | 113 | 139 | 175.75 | 45 | 0.33% |
| CCL8 | Monocyte Chemotactic Protein 2 (MCP-2) | pg/mL | Continuous | 21 | 27 | 33.5 | 8.6 | 0.33% |
| IgA | Immunoglobulin A (IgA) | mg/mL | Continuous | 1.4 | 2 | 2.8 | 0.056 | 0.33% |
| ANGPT1 | Angiopoietin-1 (ANG-1) | ng/mL | Continuous | 5.3 | 7 | 9.3 | 2.1 | 0.50% |
| BDNF | Brain-Derived Neurotrophic Factor (BDNF) | ng/mL | Continuous | 1.5 | 3 | 5.5 | 0.062 | 0.50% |
| CKM_CKB | Creatine Kinase-MB (CK-MB) | ng/mL | Continuous | 0.97 | 1.4 | 2.1 | 0.35 | 0.50% |
| MDK | Midkine | ng/mL | Continuous | 1.6 | 2 | 2.5 | 0.46 | 0.66% |
| KITLG | Stem Cell Factor (SCF) | pg/mL | Continuous | 237 | 301 | 367 | 119 | 0.83% |
| SERPINE1 | Plasminogen Activator Inhibitor 1 (PAI-1) | ng/mL | Continuous | 21 | 34 | 49.5 | 2.8 | 0.83% |
| CXCL5 | Epithelial-Derived Neutrophil-Activating Protein 78 (ENA-78) | ng/mL | Continuous | 0.39 | 0.7 | 1.2 | 0.084 | 1.00% |

TABLE 7-continued

Biomarkers in COPDGene biomarker study*

| Biomarker Abv. | Biomarker name | Units | Variable type | 25th Percentile | Median | 75$^{th}$ Percentile | LLOQ | % below LLOQ |
|---|---|---|---|---|---|---|---|---|
| VWF | von Willebrand Factor (vWF) | ug/mL | Continuous | 58 | 77 | 102 | 25 | 1.16% |
| RAGE | Receptor for advanced glycosylation end products (RAGE) | ng/mL | Continuous | 1.4 | 2.2 | 3.6 | 0.35 | 1.33% |
| HGF | Hepatocyte Growth Factor (HGF) | ng/mL | Continuous | 4.1 | 5.6 | 6.8 | 1.0 | 1.33% |
| IL8 | Interleukin-8 (IL-8) | pg/mL | Continuous | 7.3 | 9.4 | 13 | 4.0 | 1.33% |
| VEGFA | Vascular Endothelial Growth Factor (VEGF) | pg/mL | Continuous | 92 | 115 | 149 | 50 | 1.33% |
| HP | Haptoglobin | mg/mL | Continuous | 0.935 | 1.4 | 2 | 0.064 | 1.49% |
| CCL13 | Monocyte Chemotactic Protein 4 (MCP-4) | pg/mL | Continuous | 1340 | 1640 | 2130 | 972 | 2.65% |
| FAS | FASLG Receptor (FAS) | ng/mL | Continuous | 11 | 15 | 20 | 5.8 | 3.48% |
| LTF | Lactoferrin (LTF) | ng/mL | Continuous | 10 | 14 | 19 | 6.4 | 4.15% |
| IFNG | Interferon gamma (IFN-gamma) | pg/mL | Continuous | 2.3 | 3.2 | 4.3 | 1.5 | 8.62% |
| IL12B | Interleukin-12 Subunit p40 (IL-12p40) | ng/mL | Binary | NA | NA | NA | 0.22 | 38.31% |
| CA9 | Carbonic anhydrase 9 (CA-9) | ng/mL | Binary | NA | NA | NA | 0.22 | 43.28% |
| IgE | Immunoglobulin E (IgE) | U/mL | Binary | NA | NA | NA | 18 | 43.62% |
| MICA | MHC class I chain-related protein A (MICA) | pg/mL | Binary | NA | NA | NA | 73 | 45.94% |
| KLK3_F | Prostate-Specific Antigen, Free (PSA-f) | ng/mL | Binary | NA | NA | NA | 0.013 | 49.75% |
| CCL11 | Eotaxin-1 | pg/mL | Binary | NA | NA | NA | 144 | 56.38% |
| IL15 | Interleukin-15 (IL-15) | ng/mL | Binary | NA | NA | NA | 0.39 | 58.37% |
| CCL20 | Macrophage Inflammatory Protein-3 alpha (MIP-3 alpha) | pg/mL | Binary | NA | NA | NA | 38 | 73.13% |
| IL23A | Interleukin-23 (IL-23) | ng/mL | Binary | NA | NA | NA | 0.68 | 75.95% |
| IL1RN | Interleukin-1 receptor antagonist (IL-1ra) | pg/mL | Binary | NA | NA | NA | 220 | 76.62% |
| MDA_LDL | Malondialdehyde-Modified Low-Density Lipoprotein (MDA-LDL) | ng/mL | Binary | NA | NA | NA | 22 | 82.42% |
| INS_intact | Proinsulin, Intact | pM | Binary | NA | NA | NA | 7.1 | 83.75% |
| INS_total | Proinsulin, Total | pM | Binary | NA | NA | NA | 34 | 83.75% |
| CCL3 | Macrophage Inflammatory Protein-1 alpha (MIP-1 alpha) | pg/mL | Binary | NA | NA | NA | 42 | 84.74% |

TABLE 7-continued

Biomarkers in COPDGene biomarker study*

| Biomarker Abv. | Biomarker name | Units | Variable type | 25th Percentile | Median | 75$^{th}$ Percentile | LLOQ | % below LLOQ |
|---|---|---|---|---|---|---|---|---|
| IL10 | Interleukin-10 (IL-10) | pg/mL | Binary | NA | NA | NA | 6.9 | 90.55% |
| IL17A | Interleukin-17 (IL-17) | pg/mL | Binary | NA | NA | NA | 2.9 | 94.03% |
| OLR1 | Lectin-Like Oxidized LDL Receptor 1 (LOX-1) | ng/mL | Binary | NA | NA | NA | 0.75 | 94.53% |
| IL1A | Interleukin-1 alpha (IL-1 alpha) | ng/mL | Excluded | NA | NA | NA | 0.0012 | 95.52% |
| TNF | Tumor Necrosis Factor alpha (TNF-alpha) | pg/mL | Excluded | NA | NA | NA | 23 | 97.68% |
| IL6 | Interleukin-6 (IL-6) | pg/mL | Excluded | NA | NA | NA | 11 | 98.18% |
| HSPD1 | Heat Shock Protein 60 (HSP-60) | ng/mL | Excluded | NA | NA | NA | 45 | 98.34% |
| LTA | Tumor Necrosis Factor beta (TNF-beta) | pg/mL | Excluded | NA | NA | NA | 9.7 | 98.51% |
| IL1B | Interleukin-1 beta (IL-1 beta) | pg/mL | Excluded | NA | NA | NA | 4.8 | 98.67% |
| IL2 | Interleukin-2 (IL-2) | pg/mL | Excluded | NA | NA | NA | 8.3 | 98.84% |
| IL7 | Interleukin-7 (IL-7) | pg/mL | Excluded | NA | NA | NA | 8.8 | 98.84% |
| IL13 | Interleukin-13 (IL-13) | pg/mL | Excluded | NA | NA | NA | 6.2 | 99.17% |
| IL12A_IL12B | Interleukin-12 Subunit p70 (IL-12p70) | pg/mL | Excluded | NA | NA | NA | 38 | 99.34% |
| IL4 | Interleukin-4 (IL-4) | pg/mL | Excluded | NA | NA | NA | 29 | 99.34% |
| CSF2 | Granulocyte-Macrophage Colony-Stimulating Factor (GM-CSF) | pg/mL | Excluded | NA | NA | NA | 88 | 99.67% |
| IL3 | Interleukin-3 (IL-3) | ng/mL | Excluded | NA | NA | NA | 0.016 | 99.83% |
| IL5 | Interleukin-5 (IL-5) | pg/mL | Excluded | NA | NA | NA | 13 | 99.83% |
| NGF | Nerve Growth Factor beta (NGF-beta) | ng/mL | Excluded | NA | NA | NA | 0.078 | 100% |
| S100B | S100 calcium-binding protein B (S100-B) | ng/mL | Excluded | NA | NA | NA | 0.50 | 100% |

*Presented is the full list of biomarkers measured in COPDGene cohort subjects. LLOQ = lower limit of quantification. Biomarkers treated as continuous variables were transformed by quantile normalization. Biomarkers with more than 10% and less than 95% of values below LLOQ were transformed into binary variables (present or absent). Biomarkers with >95% values below LLOQ were excluded from the analysis. Median values for raw measurements together with 25$^{th}$ and 75$^{th}$ percentiles are presented for continuous variables.

To perform the meta-analysis, a single variable model was fit for each of the biomarkers in Table 8 that were also identified in the TESRA study. Equivalent covariates were included for the two studies and an ordered logistic and linear regression was fit respectively for the % LAA≤-910 HU and LP15A outcomes. P-values from both studies were combined by calculating the average Z-score of the inverse normal quantiles of the two p-values to determine a combined p-value that accounted for consistent effects of the biomarker levels on emphysema severity in the two studies (Stouffer S A., The american soldier: Adjustment during army life. *Princeton University Press.* 1949). A Bonferroni adjustment was applied based on all tested markers. For Table 8, the results presented are beta coefficients and p values for multiple regression models of biomarkers and covariates associated with emphysema outcomes. % LAA=Percent low attenuation areas; LP15A=mean lung attenuation at 15$^{th}$ percentile on lung attenuation curve; HU=Hounsfield units; FEV$_1$=Forced expiratory volume in 1$^{st}$ second; RAGE=Receptor for advanced glycosylation end products; CCL20=Macrophage Inflammatory Protein-3 alpha; ICAM1=Intercellular Adhesion Molecule 1; SERPINA7=Thyroxin-binding globulin; CDH 13=Cadherin-13; CDH1=Cadherin-1; TGFB1 LAP=Latency-Associated Peptide of Transforming Growth Factor beta 1; CCL13=Monocyte Chemotactic Protein 4; TNFRSF11B=Osteoprotegerin; CCL8=Monocyte Chemotactic Protein 2; IgA=Immunoglobulin A; SORT1=Sortilin; IL2RA=Interleukin-2 receptor alpha; CCL2=Monocyte Chemotactic Protein 1; IL-12B=Interleukin-12 Subunit p40; MDA LDL=Malondialdehyde-Modified Low-Density Lipoprotein; FAS=FASLG Receptor; SFTPD=Surfactant protein D; AXL=AXL Receptor Tyrosine Kinase; CXCL10=Interferon gamma Induced Protein 10; ADIPOQ=Adiponectin; MB=Myoglobin; SOD1=Superoxide dismutase 1; NRCAM=Neuronal Cell Adhesion Molecule. # Higher LP15A values indicate less severe emphysema, so positive coefficients are associated with less severe emphysema and negative coefficients are associated with more severe emphysema unlike higher % LAA which is associated with more severe emphysema. Biomarkers not available for replication in TESRA.

Receiver operating curves (ROC) were generated for covariates alone and covariates with biomarkers with mild emphysema compared to no emphysema as the outcome. Nominal logistic regression was performed with emphysema considered mild if % LAA≤-950 HU was 5-<10% compared to no emphysema (% LAA≤-950 HU<5%).

Statistical analyses were performed using JMP 9.0 (SAS Institute, Cary, N.C.) and R (version 3.0.2) statistical software packages (Murdoch D R., et al. Breathing new life into pneumonia diagnostics. *J Clin Microbiol.* November 2009; 47(11):3405-3408).

Results

Study Population

Demographics, physiology, quantitative HRCT measurements and patient-reported outcomes for COPDGene and TESRA cohorts are listed in Table 9. In the COPDGene biomarker study, there were 588 individuals with complete data available. Subjects with COPD were significantly older, had lower BMI, higher pack-year history of smoking and worse SGRQ scores compared to those without COPD

TABLE 8

Biomarkers and covariates associated with radiological emphysema in the COPDGene cohort (using multiple regression).*

| | % LAA ≤ -950 HU | | % LAA ≤ -910 HU | | LP15A# | |
|---|---|---|---|---|---|---|
| | Beta coefficient | p-value | Beta coefficient | p-value | Beta coefficient | p-value |
| Covariate | | | | | | |
| FEV1 (% predicted) | -0.07 | $2.9 \times 10^{-40}$ | -0.05 | $6.4 \times 10^{-29}$ | 0.42 | $2.1 \times 10^{-47}$ |
| Body mass index | -0.15 | $3.2 \times 10^{-10}$ | -0.26 | $8.2 \times 10^{-22}$ | 1.37 | $3.4 \times 10^{-21}$ |
| Current active smoking | -1.16 | $9.1 \times 10^{-5}$ | -0.76 | $1.3 \times 10^{-7}$ | 4.56 | $7.5 \times 10^{-7}$ |
| Male gender | 0.35 | 0.002 | 0.71 | $7.3 \times 10^{-9}$ | -9.57 | 0.0001 |
| Age at enrollment | 0.04 | 0.039 | 0.04 | 0.006 | -0.20 | 0.039 |
| Biomarker | | | | | | |
| RAGE | -0.69 | $2.6 \times 10^{-8}$ | -1.10 | 0.005 | 10 | 0.0002 |
| CCL20 (presence) | -0.45 | 0.0006 | -0.35 | 0.004 | 2.12 | 0.009 |
| ICAM1 | -0.42 | 0.001 | -2.40 | 0.007 | 28.39 | $3.4 \times 10^{-6}$ |
| SERPINA7¶ | 0.28 | 0.013 | 2.11 | 0.042 | -13.69 | 0.038 |
| CDH13¶ | 0.29 | 0.025 | 2.62 | 0.005 | -16.91 | 0.008 |
| CDH1¶ | -0.25 | 0.039 | -2.04 | 0.006 | 13.09 | 0.006 |
| TGFB1 LAP | -0.54 | 0.0002 | | | | |
| CCL13 | 0.35 | 0.013 | | | | |
| TNFRSF11B | 0.34 | 0.016 | | | | |
| CCL8 | -0.27 | 0.023 | | | | |
| IgA | -0.25 | 0.03 | | | 6.09 | 0.025 |
| SORT1 | -0.26 | 0.038 | | | | |
| IL2RA | 0.27 | 0.044 | | | | |
| CCL2 | 0.25 | 0.045 | | | | |
| IL12B (presence) | 0.22 | 0.049 | | | | |
| MDA LDL (absence)¶ | | | 0.33 | 0.016 | -2.07 | 0.025 |
| FAS | | | 1.16 | 0.016 | -8.53 | 0.014 |
| SFTPD | | | -1.16 | 0.025 | 8.34 | 0.016 |
| AXL | | | | | 17.05 | 0.002 |
| CXCL10 | | | | | -11.80 | 0.002 |
| ADIPOQ¶ | | | | | -7.26 | 0.015 |
| MB¶ | | | | | -7.97 | 0.016 |
| SOD1 | | | | | 11.08 | 0.009 |
| NRCAM¶ | | | | | -9.26 | 0.017 |

(p<0.01, all comparisons). The distribution of gender and current smokers was similar between non-COPD and COPD groups. The following variables were associated with emphysema (LAA≤-950 HU): lower $FEV_1$ (p<0.001), lower body mass index (p<0.001), male gender (p=0.002), older age at enrollment (p=0.038) and current non-smoking status (p<0.001); these variables were used as covariates for multiple regression (Table 10).

TABLE 9

Demographics of individuals in COPDGene and TESRA studies*

| | COPDGene (n = 588) | | | TESRA |
|---|---|---|---|---|
| | No COPD n = 247 | COPD n = 341 | p-value | COPD (n = 388) |
| Demographics | | | | |
| Age (years) | 61 ± 3 | 65 ± 0.5 | p < 0.01 | 66.6 ± 0.4 |
| Gender (male/female) | 124/123 | 178/163 | p = 0.63 | 267/121 |
| Current smokers (%) | 27 | 23 | p = 0.23 | 0 |
| Smoking History (pack-years) | 38 ± 1 | 54 ± 2 | p < 0.001 | 48 ± 1 |
| Body mass index (kg/m²) | 28.9 ± 2.3 | 27.8 ± 0.3 | p = 0.009 | 26 ± 0.2 |
| Physiology | | | | |
| $FEV_1$ post bronchodilator (% predicted) | 98 ± 3.6 | 47 ± 1 | p < 0.001 | 50 ± 0.5 |
| FVC post bronchodilator (% predicted) | 96 ± 3.6 | 79 ± 1 | p < 0.001 | 93 ± 0.9 |
| HRCT measurements | | | | |
| Average % LAA ≤ -950 HU | 2.3 ± 1.6 | 15 ± 0.7 | p < 0.001 | N/A |
| % Emphysema < 5% | 85 | 31 | | N/A |
| % Emphysema 5-<10% | 13 | 15 | | N/A |
| % Emphysema 10-<20% | 2 | 25 | | N/A |
| % Emphysema ≥ 20% | 0 | 29 | | N/A |
| Average % LAA ≤ -910 HU | 22.6 ± 3.7 | 39 ± 0.7 | p < 0.001 | 40.7 ± 0.8 |
| % Emphysema < 35% | 79 | 35 | | |
| % Emphysema 35-<45% | 15 | 19 | | |
| % Emphysema 45-<55% | 5 | 19 | | |
| % Emphysema ≥ 55% | 1 | 27 | | |
| Average LP15A | -916 ± 4.3 | -944 ± 1.3 | p < 0.001 | -945 ± 1.3 |
| Patient-reported outcomes | | | | |
| MRC dyspnea score | 0.5 ± 0.1 | 2.2 ± 0.1 | p < 0.001 | 2.0 ± 0.03 |
| SGRQ | 12 ± 3.9 | 39 ± 1.1 | p < 0.001 | 46 ± 0.8 |

*Presented are the means ± standard errors for COPDGene cohort and TESRA cohort. p values represent difference between no COPD and COPD groups for COPDGene. $FEV_1$ = Forced expiratory volume at one second; FVC = forced vital capacity; LAA = low area attenuation; N/A = data not available; LP15A = mean lung attenuation value at the 15$^{th}$ percentile on lung attenuation curve. MRC = Medical Research Council; SGRQ = St. George's Respiratory Questionnaire.

TABLE 10

Demographics of COPDGene cohort

| | COPDGene (n = 588) | | | | | |
|---|---|---|---|---|---|---|
| | | ≥5% LAA < -950 HU (n = 273) | | | | p Value |
| | <5% LAA < -950 HU (n = 315) | 5-10% (n = 82) | 10-20% (n = 91) | >20% (n = 100) | Total ≥5% | (<%5 vs. ≥5%) |
| Demographics | | | | | | |
| Age (years) | 61 ± 0.5 | 64 ± 1 | 67 ± 0.7 | 66 ± 0.8 | 66 ± 0.5 | p < 0.01 |
| Gender (male/female) | 142/173 | 49/33 | 52/39 | 59/41 | 160/113 | p < 0.001 |
| Current smokers (%) | 33 | 29 | 12 | 8 | 16 | p < 0.01 |

TABLE 10-continued

Demographics of COPDGene cohort

| | COPDGene (n = 588) | | | | | p Value |
|---|---|---|---|---|---|---|
| | <5% LAA < −950 HU (n = 315) | ≥5% LAA < −950 HU (n = 273) | | | | (<%5 vs. ≥5%) |
| | | 5-10% (n = 82) | 10-20% (n = 91) | >20% (n = 100) | Total ≥5% | |
| Smoking History (pack-years) | 42 ± 1 | 50 ± 3 | 56 ± 3 | 53 ± 3 | 53 ± 2 | p < 0.01 |
| Body mass index (kg/m$^2$) | 29.5 ± 0.3 | 28.6 ± 0.6 | 28.2 ± 0.5 | 24 ± 0.4 | 26.9 ± 0.3 | P < 0.001 |
| Physiology | | | | | | |
| FEV$_1$ post bronchodilator (% predicted) | 85 ± 1.2 | 70 ± 3.2 | 47 ± 2.1 | 35 ± 1.3 | 49 ± 1.5 | P < 0.001 |
| FVC post bronchodilator (% predicted) | 90 ± 0.9 | 87 ± 2.1 | 81 ± 2.0 | 79 ± 2.2 | 82 ± 1.2 | P < 0.001 |
| COPD by GOLD (%) | 33 | 61 | 94 | 100 | 86 | P < 0.001 |
| HRCT measurements | | | | | | |
| % Emphysema Total lung (−950 HU) | 1.6 ± 0.07 | 7.2 ± 0.2 | 14.8 ± 0.3 | 31.7 ± 0.8 | 18 ± 0.7 | P < 0.001 |
| % Emphysema Total lung (−910 HU) | 19.4 ± 0.6 | 39 ± 0.9 | 45.6 ± 0.8 | 60.4 ± 0.7 | 39 ± 0.7 | P < 0.001 |
| Emphysema Total lung (LP15A) | −913 ± 0.9 | −937 ± 0.5 | −951 ± 0.5 | −972 ± 0.9 | −954 ± 0.9 | P < 0.001 |
| Patient-reported outcomes | | | | | | |
| MRC dyspnea score | 1.0 ± 0.1 | 1.5 ± 0.2 | 2.0 ± 0.1 | 2.9 ± 0.1 | 2.2 ± 0.1 | P < 0.001 |
| SGRQ | 19 ± 1.2 | 29 ± 2.7 | 38 ± 2.1 | 47 ± 1.6 | 38 ± 1.3 | P < 0.001 |

*Presented are the means ± standard errors for COPDGene cohort and TESRA cohort. LAA = low area attenuation; FEV$_1$ = Forced expiratory volume at one second; FVC = forced vital capacity; % Emphysema = % low area attenuation < −950 HU and < −910 HU on inspiration; LP15A = mean lung attenuation value at the 15$^{th}$ percentile on lung attenuation curve. MRC = Medical Research Council; SGRQ = St. George's Respiratory Questionnaire; p values represent difference between <5% emphysema (% LAA < −950 HU) group and ≥5% emphysema group.

Biomarkers Associated with Emphysema

Figure 3A:
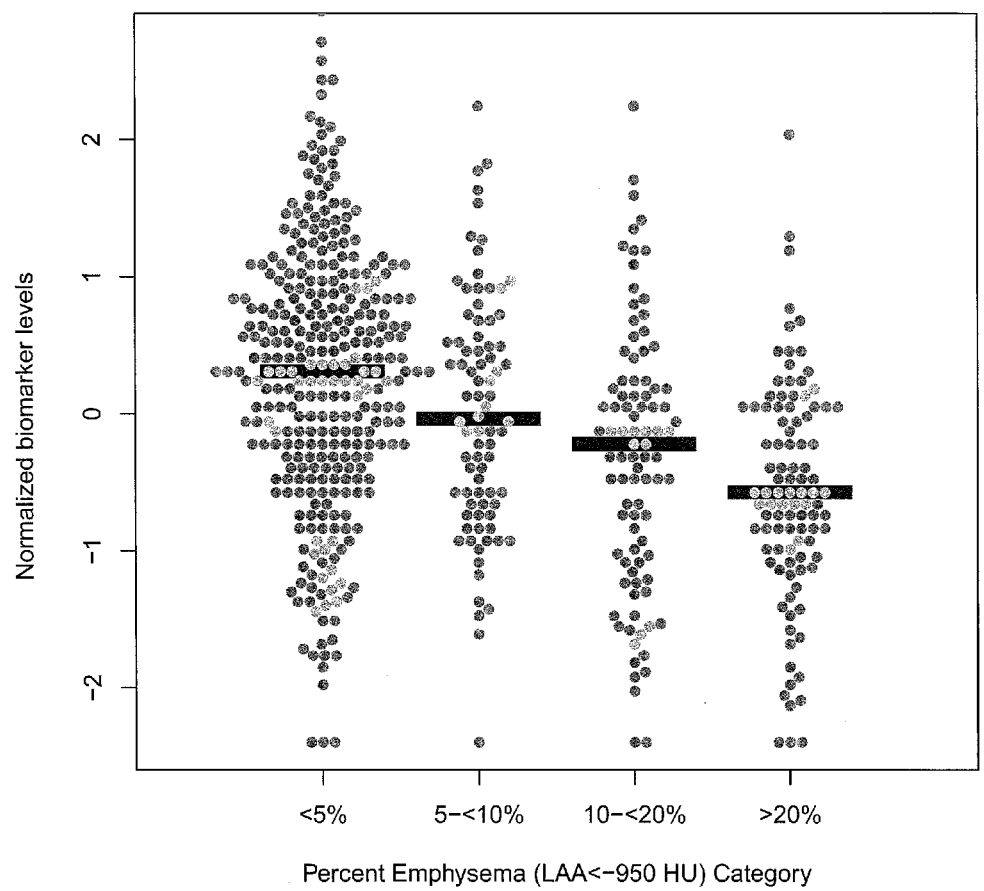
FIGS. 3A-3E show the biomarkers associated with CT-assessed emphysema in the COPDGene cohort from the COPDGene mutli-center study.
Figure 3B:
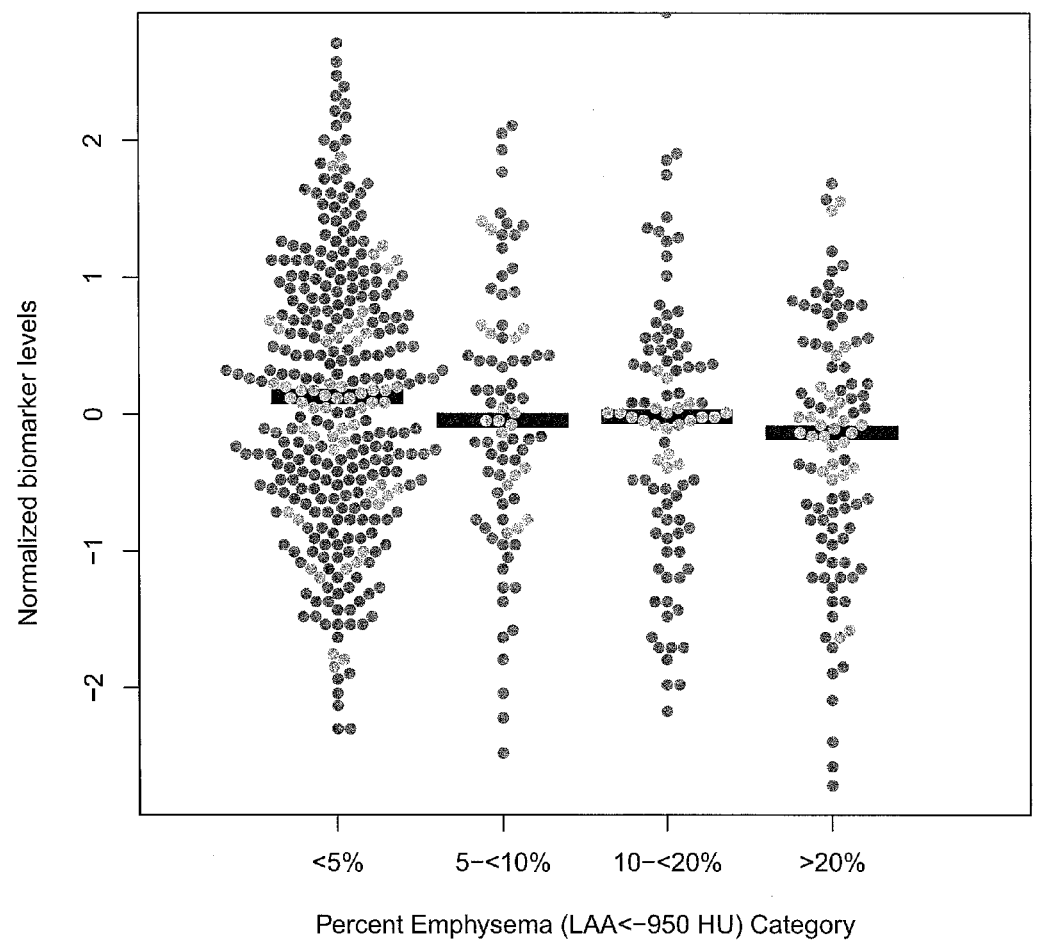
Figure 3C:
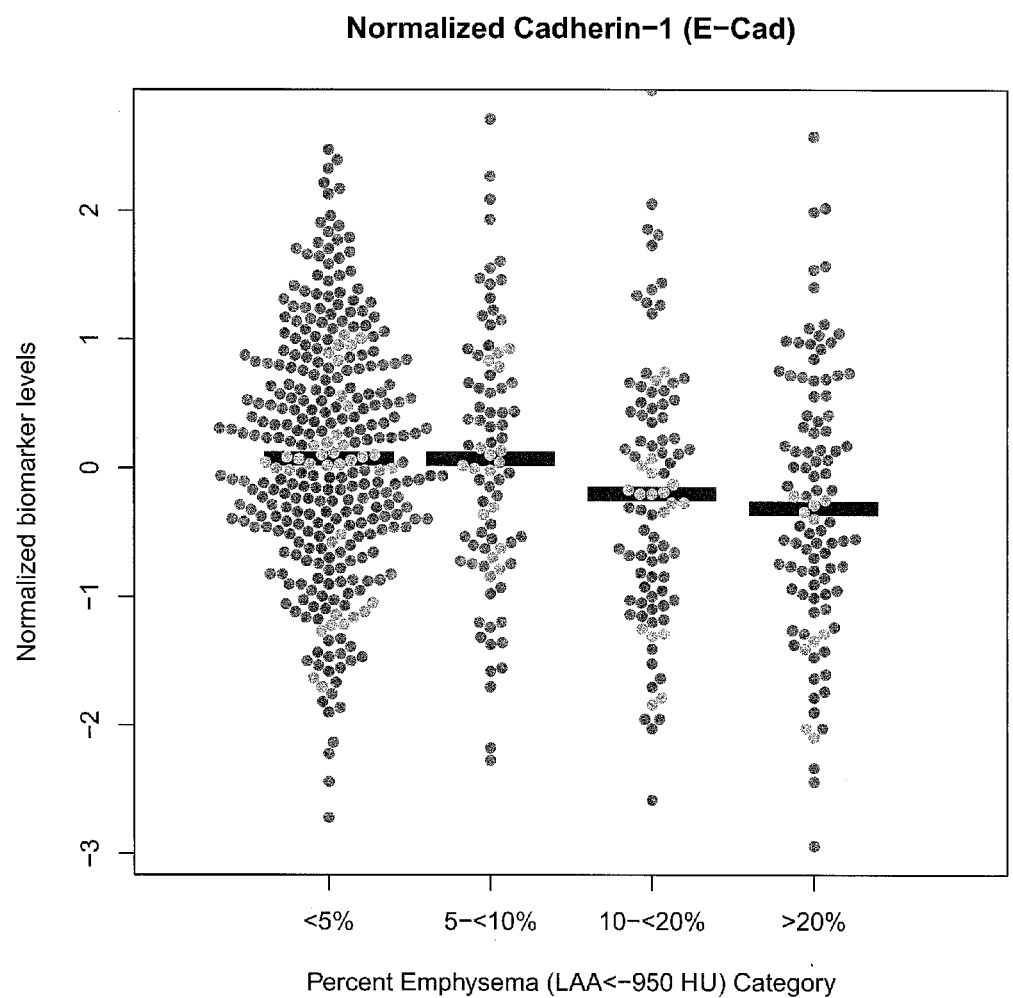
Figure 3D:
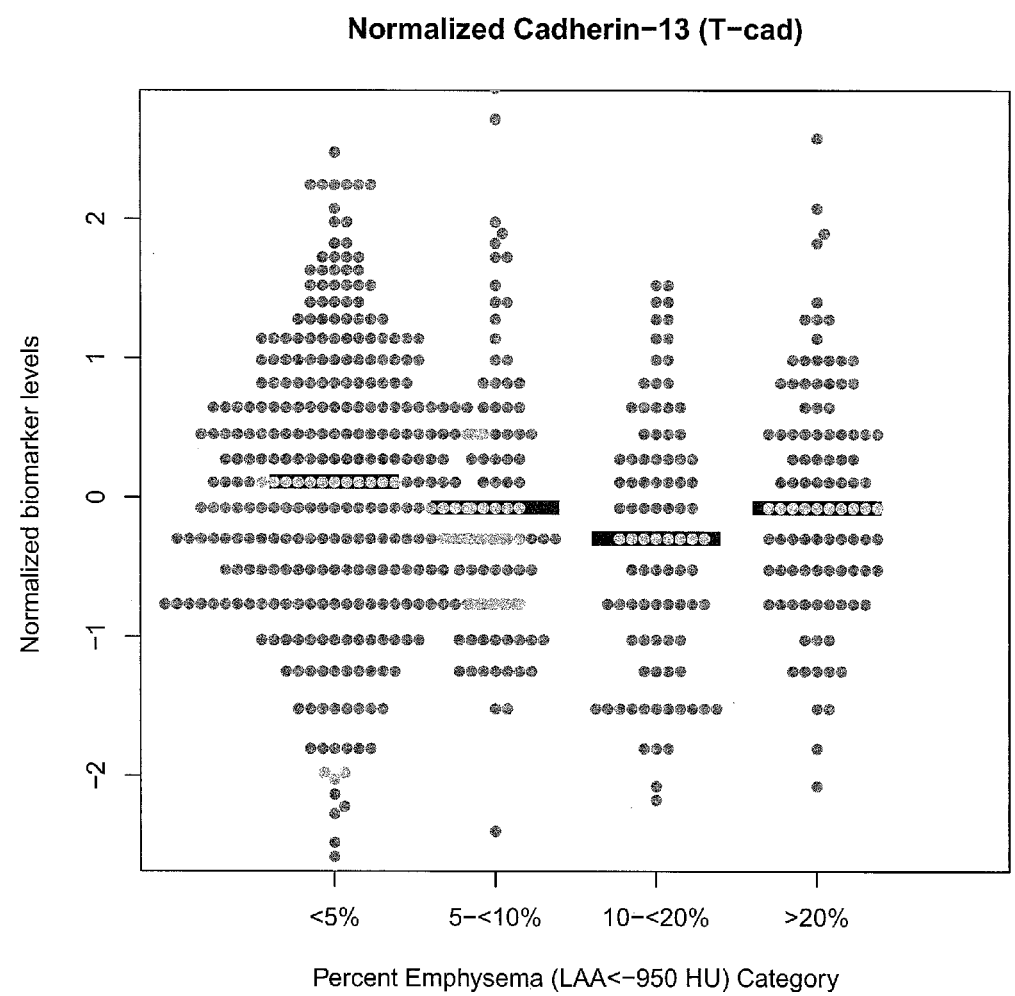
Figure 3E:
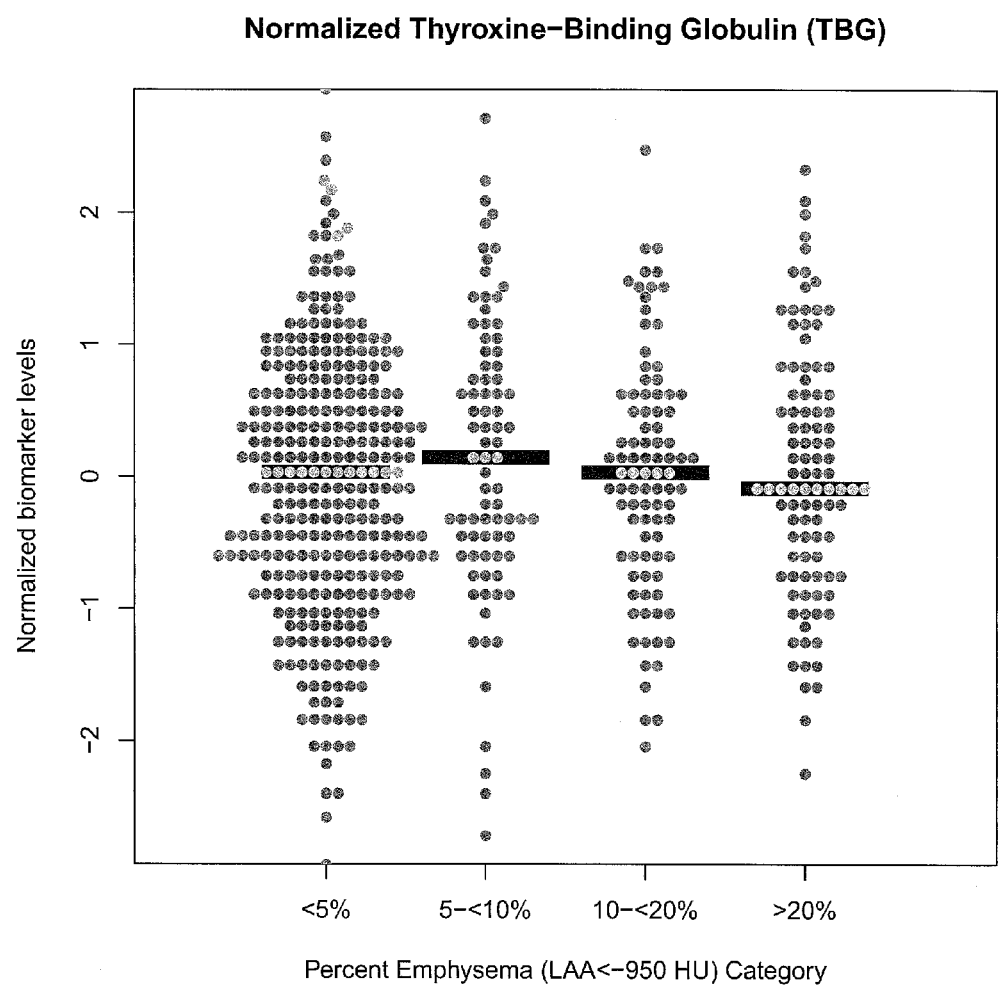
Figure 4A:
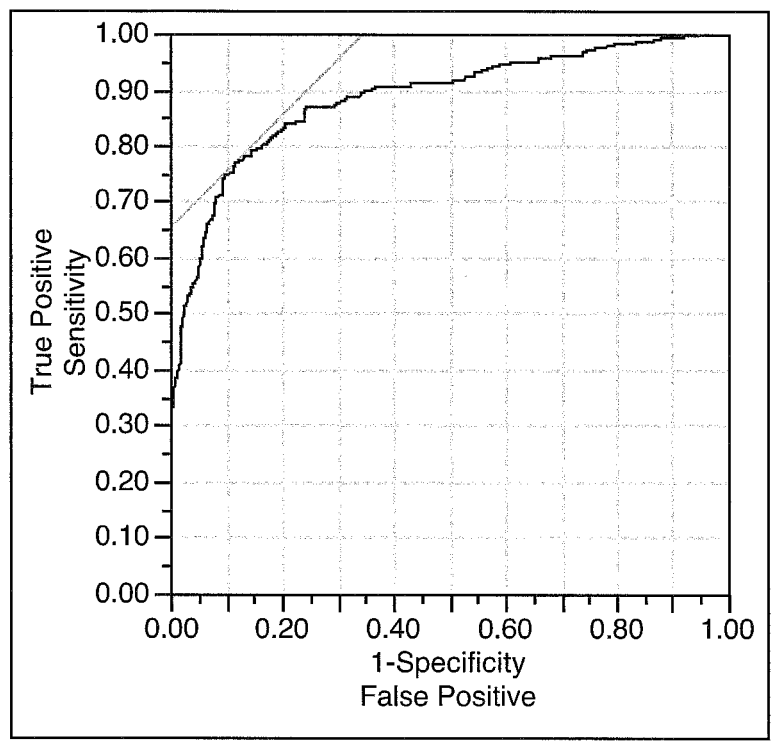
FIGS. 4A-4D show receiver operating characteristic (ROC) curves with emphysema (% LAA<-950 HU≥5%) vs. no emphysema (% LAA<-950 HU<5%) as outcome for (FIG. 4A) covariates age, gender, body mass index, smoking status and $FEV_1$ (all ranges)
Figure 4B:
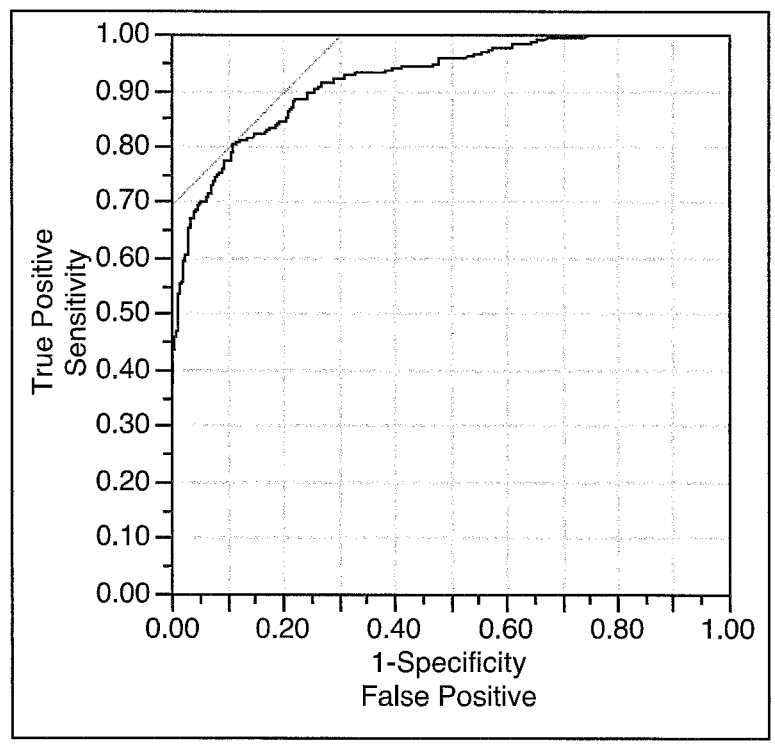
Figure 4C:
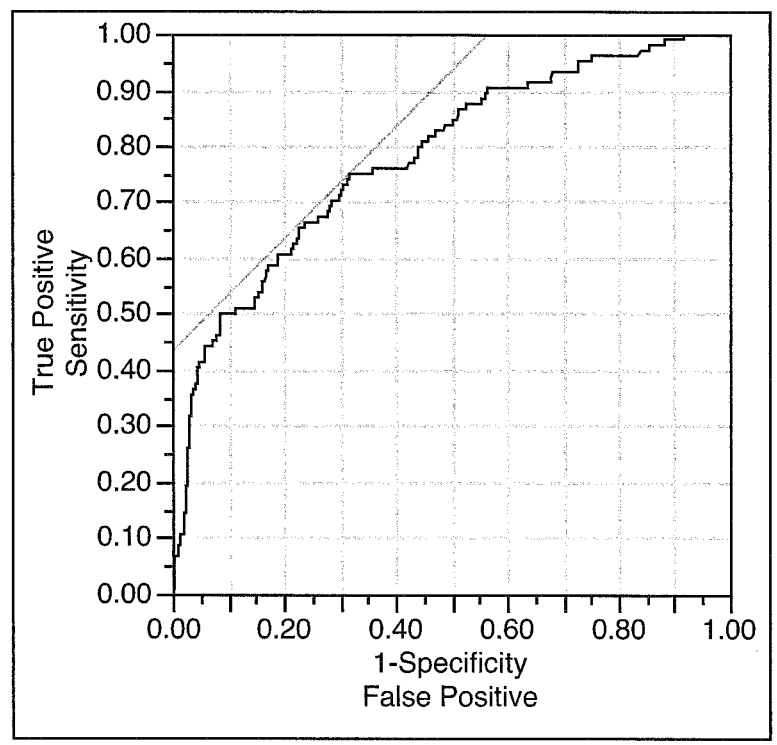
Figure 4D:
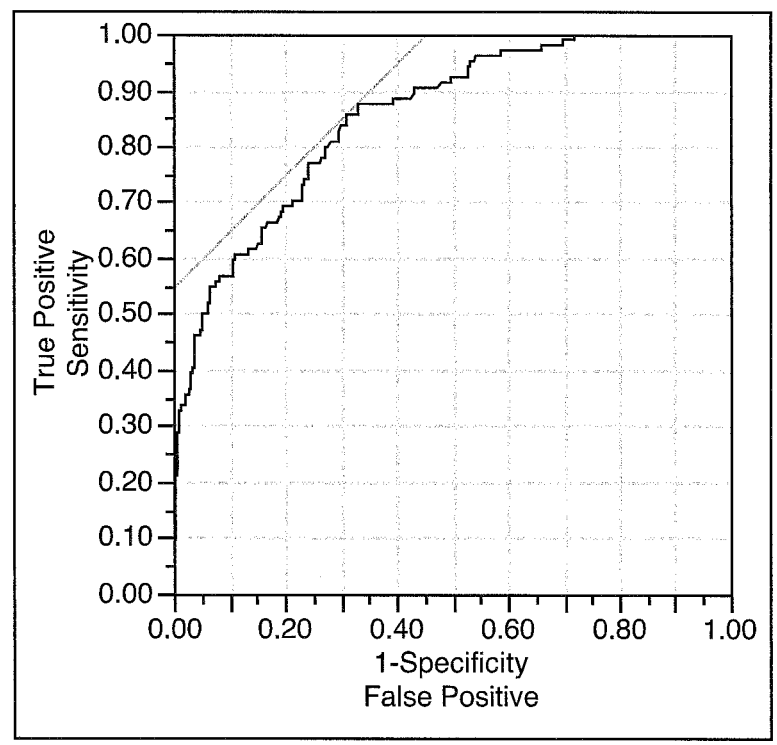

A full list of biomarkers analyzed in the COPDGene cohort is shown in Table 7. After adjusting for covariates, multiple regression analyses demonstrated a total of 24 biomarkers associated with radiologic emphysema including 15 biomarkers independently associated with % LAA≤-950 HU ($R^2$=0.4), 9 biomarkers associated with % LAA≤-910 HU ($R^2$=0.36) and 16 associated with LP15A ($R^2$=0.64, Table 8). There were 6 biomarkers that were associated with all 3 radiologic emphysema outcome variables. Advanced glycosylation end-product receptor (RAGE) was negatively associated with more severe emphysema (FIG. 3A). In addition, intercellular adhesion molecule 1 (ICAM1, FIG. 3B), macrophage inhibitory protein 3a (CCL20) and cadherin 1 (CDH1, FIG. 3C) were negatively associated with emphysema severity. Cadherin 13 (CDH13, FIG. 3D) and thyroxin-binding globulin (SERPINA7, FIG. 3E) were positively correlated with emphysema severity (p<0.001 for all comparisons). There were 3 biomarkers surfactant associated protein D (SFPD), FAS ligand receptor (FAS), and malondialdehyde-modified low-density lipoprotein (MDA LDL) associated with both % LAA≤-910 HU and LP 15 emphysema outcomes (Table 8).

Validation of Emphysema Biomarkers

Using similar statistical methods (modeling, covariates, etc), statistically significant biomarkers using an independent cohort from the TESRA study were validated. Although % LAA≤-910 HU and LP15A HRCT data were available in the TESRA cohort, % LAA≤-950 HU measurements were not. Therefore, of the total 16 biomarkers statistically associated with the emphysema outcomes ≤-910 and LP15A in the COPDGene cohort, 9 biomarkers were available for validation in TESRA cohort. After meta-analysis and adjustment for multiple testing, biomarkers RAGE (p=1.2×10$^{-9}$) and ICAM1 (p=1.5×10$^{-7}$) were associated with % LAA<-910 HU (Table 11). Similarly, with regard to the LP15A emphysema outcome variable, meta-analysis with the TESRA cohort validated the association of RAGE (p=2.5×10$^{-10}$), ICAM1 (p=6.0×10$^{-11}$), and AXL (p=3.8×10$^{-3}$) with radiologic emphysema independent of covariates (Table III). CCL20 was significantly negatively associated with emphysema in both the TESRA and COPDGene cohorts; however, meta-analysis was not possible due to CCL20 being binary in COPDGene and continuous in TESRA. Biomarkers significant in the COPDGene study such as CDH1, CDH13, SERPINA7, MDA LDL, MB, NRCAM, and ADIPOQ were not measured in the TESRA study and therefore could not be included in the meta-analysis.

TABLE 11

Meta-analysis of biomarkers associated with emphysema in COPDGene and TESRA cohorts*

| Variable | COPDGene | | TESRA | | Adjusted meta-analysis p-value |
|---|---|---|---|---|---|
| | Beta coefficient | p-value° | Beta coefficient | p-value° | |
| Percent LAA ≤−910 HU | | | | | |
| RAGE | −1.4 | $2.6 \times 10^{-5}$ | −0.52 | $9.2 \times 10^{-7}$ | $1.2 \times 10^{-9}$ |
| ICAM1 | −3.2 | $9.2 \times 10^{-6}$ | −0.37 | $3.4 \times 10^{-4}$ | $1.5 \times 10^{-7}$ |
| CCL20# | −0.87 | $1.3 \times 10^{-4}$ | −0.29 | $2.2 \times 10^{-3}$ | N/A |
| Mean lung attenuation at 15th percentile | | | | | |
| RAGE | 10.78 | $1.3 \times 10^{-5}$ | 7.08 | $3.0 \times 10^{-8}$ | $2.5 \times 10^{-10}$ |
| ICAM1 | 32.3 | $1.1 \times 10^{-9}$ | 5.14 | $4.5 \times 10^{-5}$ | $6.0 \times 10^{-11}$ |
| AXL | 18.8 | $1.8 \times 10^{-4}$ | 2.53 | 0.038 | $3.8 \times 10^{-3}$ |
| CCL20# | 6.44 | $8.2 \times 10^{-5}$ | 4.45 | $1.3 \times 10^{-4}$ | N/A |

*Presented is the regression analysis for each biomarker with an adjusted meta-analysis p value.
LAA = low attenuation area;
RAGE = Receptor for advanced glycosylation end products;
ICAM1 = Intercellular Adhesion Molecule 1;
CCL20 = Macrophage Inflammatory Protein-3 alpha;
AXL = AXL Receptor Tyrosine Kinase;
°p values for COPDGene and TESRA are two-sided p values.
CCL20 was a binary variable in COPDGene therefore it is the presence CCL20 that is negatively associated with emphysema in COPDGene cohort, while CCL20 was a continuous variable in TESRA also associated negatively associated with more severe emphysema. Meta-analysis was not possible given difference in variables (N/A).

Receiver Operating Characteristic (ROC) curves for covariates age, gender, body mass index, current smoking status without $FEV_1$ demonstrated an area under the curve (AUC) of 0.63 for the prediction of mild emphysema. The addition of 15 biomarkers from the multiple regression model raised the AUC to 0.74. When covariates included $FEV_1$ the AUC was 0.72, however when biomarkers were added to the model, the AUC increased to 0.8 (FIGS. 4A-4D and Table 12).

TABLE 12

Area under curve (AUC) for receiver operating characteristic (ROC) curves for emphysema (% LAA <−950 HU ≥5%) vs. no emphysema (% LAA <−950 HU <5%) as outcome*

| Outcome: Emphysema yes (≥5%): no (<5%) | AUC |
|---|---|
| Covariates with $FEV_1$ (including all ranges of airflow limitation, n = 588) | |
| Age, gender, BMI, smoking status | 0.72 |
| Age, gender, BMI, smoking status, $FEV_1$ (all ranges) | 0.88 |
| Age, gender, BMI, smoking status, $FEV_1$ (all ranges), 15 biomarkers | 0.92 |
| Covariates with $FEV_1$ (excluding severe and very severe airflow limitation, n = 399) | |
| Age, gender, BMI, smoking status, $FEV_1$ (≥50% predicted) | 0.78 |
| Age, gender, BMI, smoking status, $FEV_1$ (≥50% predicted), and 15 biomarkers | 0.85 |
| Covariates with $FEV_1$ (including only severe and very severe airflow limitation, n = 189) | |
| Age, gender, BMI, smoking status, $FEV_1$ (<50% predicted) | 0.86 |
| Age, gender, BMI, smoking status, $FEV_1$ (<50% predicted) and 15 biomarkers | 0.93 |

*Presented is the area under the curve (AUC) for receiver operating characteristic curves derived for the presence of emphysema compared to no emphysema on CT scan for all individuals and separately for those without severe airflow limitation and those with severe airflow limitation.
BMI = Body mass index;
FEV1 = Forced expiratory volume in 1st second.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

REFERENCES

1. Vestbo, J., et al. Global Strategy for the Diagnosis, Management and Prevention of Chronic Obstructive Pulmonary Disease, GOLD Executive Summary. *Am J Respir Crit Care Med* (2012).
2. Hurst, J. R., et al. Susceptibility to exacerbation in chronic obstructive pulmonary disease. *N Engl J Med* 363, 1128-1138 (2010).
3. Thomsen, M., et al. Inflammatory biomarkers and exacerbations in chronic obstructive pulmonary disease. *Jama* 309, 2353-2361 (2013).
4. Agusti, A. & Faner, R. Systemic inflammation and comorbidities in chronic obstructive pulmonary disease. *Proc Am Thorac Soc* 9, 43-46 (2012).
5. Decramer, M., Janssens, W. & Miravitlles, M. Chronic obstructive pulmonary disease. *Lancet* 379, 1341-1351 (2012).
6. Rosenberg, S. R. & Kalhan, R. Biomarkers in chronic obstructive pulmonary disease. *Transl Res* 159, 228-237 (2012).
7. Thomsen, M., Dahl, M., Lange, P., Vestbo, J. & Nordestgaard, B. G. Inflammatory Biomarkers and Comorbidities in Chronic Obstructive Pulmonary Disease. *Am J Respir Crit Care Med* (November 2012) November; 186(10): 982-988.
8. Gaki, E., et al. Associations between BODE index and systemic inflammatory biomarkers in COPD. *Copd* 8, 408-413 (2011).
9. Ozyurek, B. A., Ulasli, S. S., Bozbas, S. S., Bayraktar, N. & Akcay, S. Value of serum and induced sputum surfactant protein-D in chronic obstructive pulmonary disease. *Multidisciplinary respiratory medicine* 8, 36 (2013).
10. Bafadhel, M., et al. Acute exacerbations of chronic obstructive pulmonary disease: identification of biologic clusters and their biomarkers. *Am J Respir Crit Care Med* 184, 662-671 (2011).
11. Singh, D., Edwards, L., Tal-Singer, R. & Rennard, S. Sputum neutrophils as a biomarker in COPD: findings from the ECLIPSE study. *Respir Res* 11, 77 (2010).
12. Minas, M., et al. Fetuin-A is associated with disease severity and exacerbation frequency in patients with COPD. *COPD* 10, 28-34 (2013).
13. Nikolakopoulou, S., et al. Serum Angiopoietin-2 and CRP Levels During COPD Exacerbations. *COPD* (2013).
14. Gao, P., et al. Sputum inflammatory cell-based classification of patients with acute exacerbation of chronic obstructive pulmonary disease. *PLoS One* 8, e57678 (2013).
15. Tofan, F., Rahimi-Rad, M. H., Rasmi, Y. & Rahimirad, S. High sensitive C-reactive protein for prediction of adverse outcome in acute exacerbation of chronic obstructive pulmonary disease. *Pneumologia* 61, 160-162 (2012).
16. Bartziokas, K., et al. Serum uric acid on COPD exacerbation as predictor of mortality and future exacerbations. *Eur Respir J* (2013).
17. Ju, C. R., Liu, W. & Chen, R. C. Serum surfactant protein D: biomarker of chronic obstructive pulmonary disease. *Dis Markers* 32, 281-287 (2012).
18. Hoiseth, A. D., Omland, T., Hagve, T. A., Brekke, P. H. & Soyseth, V. NT-proBNP independently predicts long term mortality after acute exacerbation of COPD—a prospective cohort study. *Respir Res* 13, 97 (2012).
19. Karadag, F., Karul, A. B., Cildag, O., Yilmaz, M. & Ozcan, H. Biomarkers of systemic inflammation in stable and exacerbation phases of COPD. *Lung* 186, 403-409 (2008).
20. Perera, W. R., et al. Inflammatory changes, recovery and recurrence at COPD exacerbation. *Eur Respir J* 29, 527-534 (2007).
21. Hurst, J. R., Perera, W. R., Wilkinson, T. M., Donaldson, G. C. & Wedzicha, J. A. Systemic and upper and lower airway inflammation at exacerbation of chronic obstructive pulmonary disease. *Am J Respir Crit Care Med* 173, 71-78 (2006).
22. Higashimoto, Y., et al. Increased serum concentrations of tissue inhibitor of metalloproteinase-1 in COPD patients. *Eur Respir J* 25, 885-890 (2005).
23. Gerritsen, W. B., Asin, J., Zanen, P., van den Bosch, J. M. & Haas, F. J. Markers of inflammation and oxidative stress in exacerbated chronic obstructive pulmonary disease patients. *Respir Med* 99, 84-90 (2005).
24. Tug, T., Karatas, F. & Terzi, S. M. Antioxidant vitamins (A, C and E) and malondialdehyde levels in acute exacerbation and stable periods of patients with chronic obstructive pulmonary disease. *Clinical and investigative medicine. Medecine clinique et experimentale* 27, 123-128 (2004).
25. Rohde, G., et al. Soluble interleukin-5 receptor alpha is increased in acute exacerbation of chronic obstructive pulmonary disease. *Int Arch Allergy Immunol* 135, 54-61 (2004).
26. Bhatt, S. P., Khandelwal, P., Nanda, S., Stoltzfus, J. C. & Fioravanti, G. T. Serum magnesium is an independent predictor of frequent readmissions due to acute exacerbation of chronic obstructive pulmonary disease. *Respir Med* 102, 999-1003 (2008).
27. Carolan, B. J., et al. The association of adiponectin with computed tomography phenotypes in chronic obstructive pulmonary disease. *Am J Respir Crit Care Med* 188, 561-566 (2013).
28. Regan, E. A., et al. Genetic epidemiology of COPD (COPDGene) study design. *COPD* 7, 32-43 (2010).
29. Fabbri, L. M. & Hurd, S. S. Global Strategy for the Diagnosis, Management and Prevention of COPD: 2003 update. *Eur Respir J* 22, 1-2 (2003).
30. Washko, G. R., et al. Lung volumes and emphysema in smokers with interstitial lung abnormalities. *N Engl J Med* 364, 897-906 (2011).
31. Fletcher C M, Gilson, J. G., Hugh-Jones, P., Scadding, J. G. . Terminology, definitions, and classification of chronic pulmonary emphysema and related conditions. *Thorax.* 1959;14.
32. Mohamed Hoesein F A, Zanen P, Boezen H M, et al. Lung function decline in male heavy smokers relates to baseline airflow obstruction severity. *Chest.* December 2012;142(6):1530-1538.
33. Li Y, Swensen S J, Karabekmez L G, et al. Effect of emphysema on lung cancer risk in smokers: a computed tomography-based assessment. *Cancer Prev Res* (Phila). January 2011;4(1):43-50.
34. de Torres J P, Bastarrika G, Wisnivesky J P, et al. Assessing the relationship between lung cancer risk and emphysema detected on low-dose CT of the chest. *Chest.* December 2007;132(6):1932-1938.
35. Haruna A, Muro S, Nakano Y, et al. CT scan findings of emphysema predict mortality in COPD. *Chest.* September 2010;138(3):635-640.
36. Bastarrika G, Wisnivesky J P, Pueyo J C, et al. Low-dose volumetric computed tomography for quantification of emphysema in asymptomatic smokers participating in an early lung cancer detection trial. *J Thorac Imaging.* August 2009;24(3):206-211.
37. Kirby M, Coxson H O. Computed tomography biomarkers of pulmonary emphysema. *Copd.* August 2013;10(4):547-550.
38. Schroeder J D, McKenzie A S, Zach J A, et al. Relationships between airflow obstruction and quantitative CT measurements of emphysema, air trapping, and airways in subjects with and without chronic obstructive pulmonary disease. *AJR Am J Roentgenol.* September 2013;201(3):W460-470.
39. Mendoza C S, Washko G R, Ross J C, et al. Emphysema Quantification in a Multi-Scanner Hrct Cohort Using Local Intensity Distributions. *Proc IEEE Int Symp Biomed Imaging.* 2013:474-477.
40. Parr D G, Dirksen A, Piitulainen E, Deng C, Wencker M, Stockley R A. Exploring the optimum approach to the use of CT densitometry in a randomised placebo-controlled study of augmentation therapy in alpha 1-antitrypsin deficiency. *Respir Res.* 2009;10:75.
41. Stoller J K, Aboussouan L S. A review of alpha1-antitrypsin deficiency. *Am J Respir Crit Care Med.* Feb. 1, 2012;185(3):246-259.
42. Cheng D T, Kim D K, Cockayne D A, et al. Systemic soluble receptor for advanced glycation endproducts is a biomarker of emphysema and associated with AGER genetic variants in patients with chronic obstructive pulmonary disease. *Am J Respir Crit Care Med.* Oct. 15, 2013;188(8):948-957.
43. Carolan B J, Kim Y I, Williams A A, et al. The association of adiponectin with computed tomography phenotypes in chronic obstructive pulmonary disease. *Am J Respir Crit Care Med.* Sep. 1, 2013;188(5):561-566.
44. Miller M, Ramsdell J, Friedman P J, Cho J Y, Renvall M, Broide D H. Computed tomographic scan-diagnosed chronic obstructive pulmonary disease-emphysema: eotaxin-1 is associated with bronchodilator response and extent of emphysema. *J Allergy Clin Immunol.* November 2007;120(5):1118-1125.
45. Gaki E, Kontogianni K, Papaioannou A I, et al. Associations between BODE index and systemic inflammatory biomarkers in COPD. *Copd.* December 2011;8(6):408-413.
46. Rosenberg S R, Kalhan R. Biomarkers in chronic obstructive pulmonary disease. *Transl Res.* April 2012;159(4):228-237.
47. Jones P W. Tesra (treatment of emphysema with selective retinoid agonist) study results. *American journal of respiratory and critical care medicine* 2011;183:A6418.
48. Han M K, Kazerooni E A, Lynch D A, et al. Chronic obstructive pulmonary disease exacerbations in the COPDGene study: associated radiologic phenotypes. *Radiology.* October 2011;261(1):274-282.
49. O'Neal W K, Anderson W, Basta P V, et al. Comparison of serum, EDTA plasma and P100 plasma for luminex-based biomarker multiplex assays in patients with chronic obstructive pulmonary disease in the SPIROMICS study. *J Transl Med.* 2014;12:9.
50. Stouffer S A. The american soldier: Adjustment during army life. *Princeton University Press.* 1949.
51. Murdoch D R, O'Brien K L, Scott J A, et al. Breathing new life into pneumonia diagnostics. *J Clin Microbiol.* November 2009;47(11):3405-3408.

52. Buckley S T, Ehrhardt C. The receptor for advanced glycation end products (RAGE) and the lung. *J Biomed Biotechnol.* 2010;2010:917108.
53. Pullerits R, Bokarewa M, Dahlberg L, Tarkowski A. Decreased levels of soluble receptor for advanced glycation end products in patients with rheumatoid arthritis indicating deficient inflammatory control. *Arthritis Res Ther.* 2005;7(4):R817-824.
54. Falcone C, Bozzini S, Guasti L, et al. Soluble RAGE plasma levels in patients with coronary artery disease and peripheral artery disease. *Scientific World Journal.* 2013; 2013:584504.
55. Alexiou P, Chatzopoulou M, Pegklidou K, Demopoulos V J. RAGE: a multi-ligand receptor unveiling novel insights in health and disease. *Curr Med Chem.* 2010;17 (21):2232-2252.
56. Uchida T, Shirasawa M, Ware L B, et al. Receptor for advanced glycation end-products is a marker of type I cell injury in acute lung injury. *Am J Respir Crit Care Med.* May 1, 2006;173(9):1008-1015.
57. Smith D J, Yerkovich S T, Towers M A, Carroll M L, Thomas R, Upham J W. Reduced soluble receptor for advanced glycation end-products in COPD. *Eur Respir J.* March 2011;37(3):516-522.
58. Cockayne D A, Cheng D T, Waschki B, et al. Systemic biomarkers of neutrophilic inflammation, tissue injury and repair in COPD patients with differing levels of disease severity. *PLoS One.* 2012;7(6):e38629.
59. Miniati M, Monti S, Basta G, Cocci F, Fornai E, Bottai M. Soluble receptor for advanced glycation end products in COPD: relationship with emphysema and chronic cor pulmonale: a case-control study. *Respir Res.* 2011;12:37.
60. Wu L, Ma L, Nicholson L F, Black P N. Advanced glycation end products and its receptor (RAGE) are increased in patients with COPD. *Respir Med.* March 2011;105(3):329-336.
61. Stogsdill M P, Stogsdill J A, Bodine B G, et al. Conditional overexpression of receptors for advanced glycation end-products in the adult murine lung causes airspace enlargement and induces inflammation. *Am J Respir Cell Mol Biol.* July 2013;49(1):128-134.
62. Di Stefano A, Maestrelli P, Roggeri A, et al. Upregulation of adhesion molecules in the bronchial mucosa of subjects with chronic obstructive bronchitis. *Am J Respir Crit Care Med.* March 1994;149(3 Pt 1):803-810.
63. El-Deek S E, Makhlouf H A, Saleem T H, Mandour M A, Mohamed N A. Surfactant protein D, soluble intercellular adhesion molecule-1 and high-sensitivity C-reactive protein as biomarkers of chronic obstructive pulmonary disease. *Med Princ Pract.* 2013;22(5):469-474.
64. Huang H, Jiang H, Kong X, et al. [Association of intercellular adhesion molecule-1 gene K469E polymorphism with chronic obstructive pulmonary disease]. *Zhong Nan Da Xue Xue Bao Yi Xue Ban.* January 2012; 37(1):78-83.
65. Lopez-Campos J L, Calero C, Arellano-Orden E, et al. Increased levels of soluble ICAM-1 in chronic obstructive pulmonary disease and resistant smokers are related to active smoking. *Biomark Med.* December 2012;6(6):805-811.
66. Aaron C P, Schwartz, J. E., Tracy, R., Hoffman, E. A., Austin, J. H. M., Oelsner, E. C., Donohue, K. M., Kalhan, R., Jacobs, D., Barr, R. G. . Intercellular Adhesion Molecule (icam)1 And Longitudinal Change In Percent Emphysema And Lung Function: The MESA Lung Study. *Am J Rspir Crit Care Med.* 2013;187:A1523.
67. Dieu-Nosjean M C, Massacrier C, Homey B, et al. Macrophage inflammatory protein 3alpha is expressed at inflamed epithelial surfaces and is the most potent chemokine known in attracting Langerhans cell precursors. *J Exp Med.* Sep. 4 2000;192(5):705-718.
68. Meuronen A, Majuri M L, Alenius H, et al. Decreased cytokine and chemokine mRNA expression in bronchoalveolar lavage in asymptomatic smoking subjects. *Respiration.* 2008;75(4):450-458.
69. Bracke K R, D'Hulst A I, Maes T, et al. Cigarette smoke-induced pulmonary inflammation and emphysema are attenuated in CCR6-deficient mice. *J Immunol.* Oct. 1, 2006;177(7):4350-4359.
70. Gall T M, Frampton A E. Gene of the month: E-cadherin (CDH1). *J Clin Pathol.* November 2013;66(11):928-932.
71. Milara J, Peiro T, Serrano A, Cortijo J. Epithelial to mesenchymal transition is increased in patients with COPD and induced by cigarette smoke. *Thorax.* May 2013;68(5):410-420.
72. Tsuduki K N H, Nakajima, T., Tsujimura, S., Yoshida, S., Takahashi, E., Nakamura, M., Minematsu, N., Tateno, H., Ishizaka, A. Genetic polymorphism of e-cadherin and copd. *Am J Respir Crit Care Med.* 2009;179:A2999.
73. Kasahara D I, Williams, A. S., Benedito, L. A., Ranschr, B., Kobzik, L., Hug, C., Shore, S. A. Role of the adiponectin binding protein, t-cadherin (cdh13), in pulmonaryt responses to subacute ozone. *PLoS One.* 2013;8: e65829.
74. Takeuchi T, Misaki, A., Fujita, J., Sonobe, H., Ohtsuki, Y. T-cadherin (cdh13, h-cadherin) expression downregulated surfactant protein d in bronchioloalveolar cells. *Virchows Archiv: and international journal of pathology.* 2001;438:370-375.

What is claimed is:

1. A method of identifying and treating a subject at risk of exacerbation of chronic obstructive pulmonary disease (COPD) comprising:
   a. obtaining a biological sample from the subject;
   b. determining the expression level of each protein in a protein panel consisting of CCL24, IL2 RA, APOA4, GC, IgA, LPA, KLK3 F, FAS, NRCAM, TNFRSF10 C, IL12 B, and IL23 A in the biological sample from the subject;
   c. identifying the subject as at risk of exacerbation when the expression level of each of the proteins in the protein panel from the sample is altered as compared to the expression of level of the same proteins from a control, wherein the altered expression level is at least about 5% increased or decreased from the expression level of the control; and
   d. administering to the subject identified in step (c) a compound selected from the group consisting of corticosteroids, steroids, antibiotics, and combinations thereof.

2. The method of claim 1, wherein the biological sample is selected from the group consisting of blood, plasma, and peripheral blood mononuclear cells (PBMCs).

* * * * *

UNITED STATES PATENT AND TRADEMARK OFFICE
CERTIFICATE OF CORRECTION

PATENT NO.       : 9,952,225 B2
APPLICATION NO.  : 15/113593
DATED            : April 24, 2018
INVENTOR(S)      : Russell P. Bowler It is certified that error appears in the above-identified patent and that said Letters Patent is hereby corrected as shown below:

In the Claims

In Claim 1, Column 56, Lines 43-47, please delete "b. determining the expression level of each protein in a protein panel consisting of CCL24, IL2 RA, APOA4, GC, IgA, LPA, KLK3 F, FAS, NRCAM, TNFRSF10 C, IL12 B, and IL23 A in the biological sample from the subject;"

And insert --b. determining the expression level of each protein in a protein panel consisting of CCL24, IL2RA, APOA4, GC, IgA, LPA, KLK3_F, FAS, NRCAM, TNFRSF10C, IL12B, and IL23A in the biological sample from the subject;--

Signed and Sealed this
Twenty-sixth Day of June, 2018

Andrei Iancu
*Director of the United States Patent and Trademark Office*